US006928280B1

(12) United States Patent
Xanthos et al.

(10) Patent No.: US 6,928,280 B1
(45) Date of Patent: Aug. 9, 2005

(54) METHOD AND SYSTEM FOR MEASURING DATA QUALITY OF SERVICE IN A WIRELESS NETWORK USING MULTIPLE REMOTE UNITS AND A BACK END PROCESSOR

(75) Inventors: James Xanthos, Laurel, MD (US);
Mark McDowell, Alexandria, VA (US);
Graham Stead, Arlington, VA (US);
Joseph Khalil, Alexandria, VA (US);
David Helinski, Arlington, VA (US);
Joseph Kitchell, Centreville, VA (US)

(73) Assignee: Telephia, Inc., San Francisco, CA (US)

( * ) Notice: Subject to any disclaimer, the term of this patent is extended or adjusted under 35 U.S.C. 154(b) by 0 days.

(21) Appl. No.: 09/550,955

(22) Filed: Apr. 17, 2000

Related U.S. Application Data

(60) Provisional application No. 60/190,691, filed on Mar. 20, 2000.

(51) Int. Cl.[7] .............................................. H04Q 7/20
(52) U.S. Cl. .................... 455/423; 455/67.11; 455/424
(58) Field of Search ................................ 455/423, 424,
455/425, 67.11, 67.13, 67.14, 67.15, 67.7,
452.2, 414.1, 456.1, 466, 446; 370/338;
709/232

(56) References Cited

U.S. PATENT DOCUMENTS

| 5,425,076 A | * | 6/1995 | Knippelmier ............ 379/27.04 |
| 5,557,748 A | | 9/1996 | Norris ..................... 395/200.1 |
| 5,644,623 A | * | 7/1997 | Gulledge .................... 455/423 |

(Continued)

FOREIGN PATENT DOCUMENTS

| EP | 0 837 615 | 4/1998 |
| EP | 0 984 645 | 3/2000 |
| FR | 2 745 144 | 8/1997 |

OTHER PUBLICATIONS

Advanced Management of Telecommunications Networks. 1991. Electrical Communication. vol. 65(1), pp. 52–59.

Ascom "Qvoice" Brochure.

TEMS™ Investigation web pages found at http://www.ericsson.com/wireless/products/tems/indes.shtml, Mar. 28, 2000.

Nemo Technologies TOM (Tool for Outdoor Measurement Version 1.0)Product description V.1.0.

Safeco Voice Print Brochure and web pages found at http://www.safco.com/measurement/voiceprint.html, Mar. 22, 2000.

(Continued)

*Primary Examiner*—Erika A. Gary
(74) *Attorney, Agent, or Firm*—Roberts Abokhair & Mardula, LLC

(57) ABSTRACT

The present invention provides for a method and system for measuring data quality of service in a wireless network using multiple peripatetic (i.e. mobile) and/or stationary, unattended, position, and performance instruments (PUPPIs) that are remotely controlled by a back end processor. In some embodiments of the invention, the data service whose quality is measured relates to wireless Internet access, e-commerce transactions, wireless messaging, or push technologies. In other embodiments of the invention, the system includes an element that is located within the wireless network infrastructure, for example, at the WAP gateway to monitor the wireless data protocol and to perform benchmarking measurements.

98 Claims, 35 Drawing Sheets

U.S. PATENT DOCUMENTS

| | | | | |
|---|---|---|---|---|
| 5,657,450 | A | | 8/1997 | Rao et al. .................... 395/610 |
| 5,675,371 | A | * | 10/1997 | Barringer .................... 725/148 |
| 5,796,952 | A | | 8/1998 | Davis et al. ............ 395/200.54 |
| 5,842,224 | A | | 11/1998 | Fenner ........................ 711/202 |
| 5,884,244 | A | | 3/1999 | Phaal ......................... 702/186 |
| 5,928,306 | A | | 7/1999 | France et al. ............... 701/207 |
| 5,959,577 | A | | 9/1999 | Fan et al. .............. 342/357.13 |
| 5,987,306 | A | * | 11/1999 | Nilsen et al. .............. 455/67.1 |
| 5,987,320 | A | | 11/1999 | Bobick ........................ 455/423 |
| 6,003,079 | A | | 12/1999 | Friedrich et al. ........... 709/224 |
| 6,006,260 | A | | 12/1999 | Barrick, Jr. et al. ........ 709/224 |
| 6,012,096 | A | | 1/2000 | Link et al. .................. 709/233 |
| 6,154,776 | A | * | 11/2000 | Martin ........................ 709/226 |
| 6,167,253 | A | * | 12/2000 | Farris et al. ............. 455/412.2 |
| 6,169,896 | B1 | * | 1/2001 | Sant et al. ................... 455/424 |
| 6,385,451 | B1 | * | 5/2002 | Kalliokulju et al. ......... 455/437 |
| 6,430,397 | B1 | * | 8/2002 | Willrett .................... 455/67.11 |
| 6,445,916 | B1 | * | 9/2002 | Rahman ..................... 455/423 |
| 6,522,881 | B1 | * | 2/2003 | Feder et al. ................. 455/437 |
| 2002/0015398 | A1 | * | 2/2002 | Kikinis ........................ 370/338 |

OTHER PUBLICATIONS

Cwt baseLINE and workBENCH web pages found at http://www.comarco.com/html/fm highlights.htm, Mar. 17, 2000.

Grayson Wireless web pages found at http://www.grayson.com/surveyor.html, Mar. 22, 2000.

CELLTEST "Field Test Solutions" brochure.

Ameritech Corp. SWARM brochure web pages found at http://www.ameritec.com/databank/products/product_SWARM.html, Dec. 17, 1999.

Neopoint DataLogger–DV™ brochure.

Qualcomm's Retriever™ Pilot Scanner and Test Phone brochure, Jan. 1999.

Qualcomm's QCTest™ CAIT CDMA Air Interface Tester brochure, Aug. 1999.

Agilent "Test & Measurement" web page found at http://www.tm.agilent.com/Products/English/DriveTestandMappingSystems.html, Mar. 28, 2000.

* cited by examiner

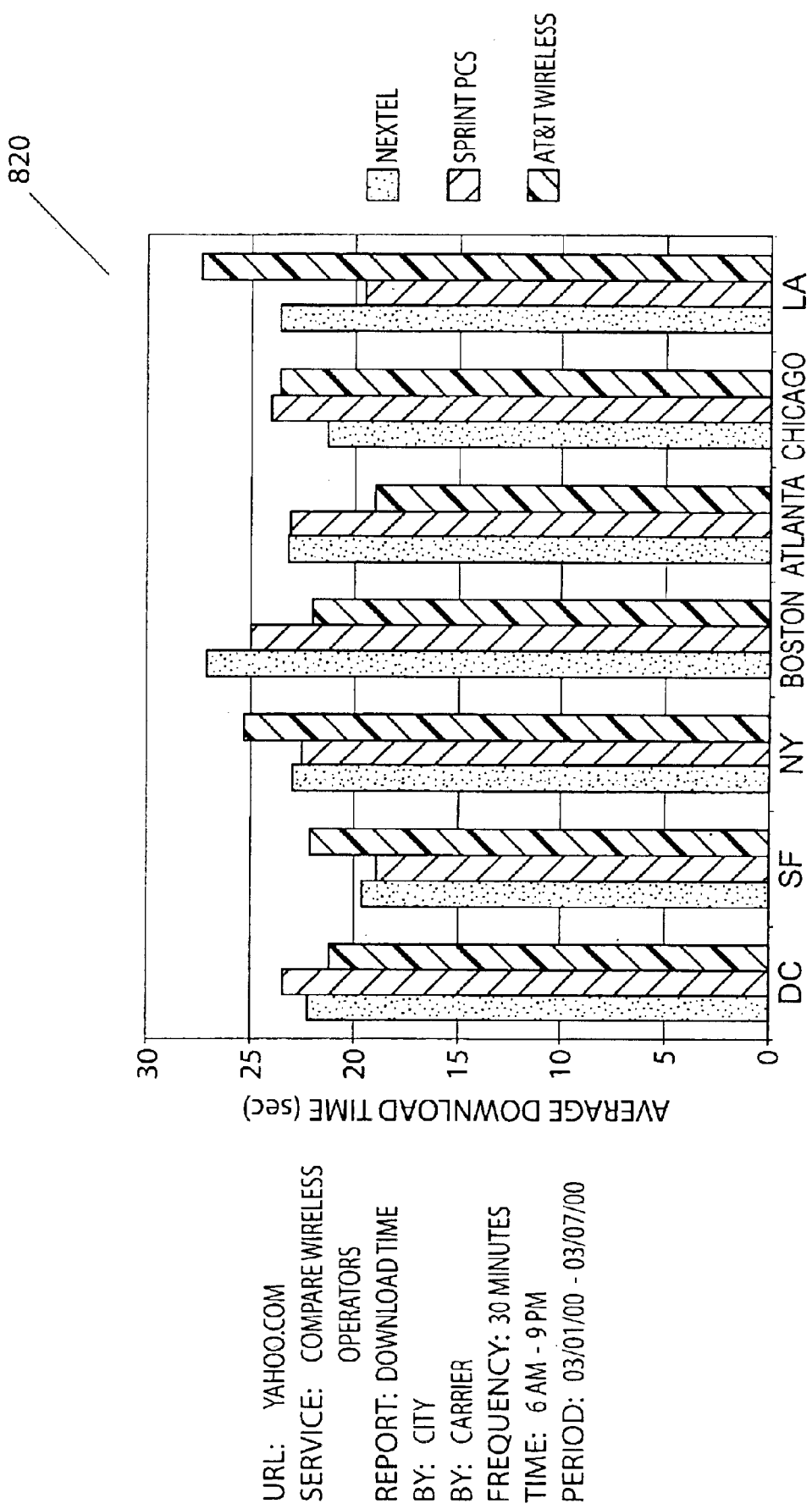

URL: YAHOO.COM
SERVICE: GATEWAY BREAKDOWN
REPORT: DOWNLOAD TIME
COMPONENTS 1
BY: CITY
CARRIER: NEXTEL
FREQUENCY: 60 MINUTES
TIME: 12 PM - 12 PM
PERIOD: 03/01/00 - 03/07/00

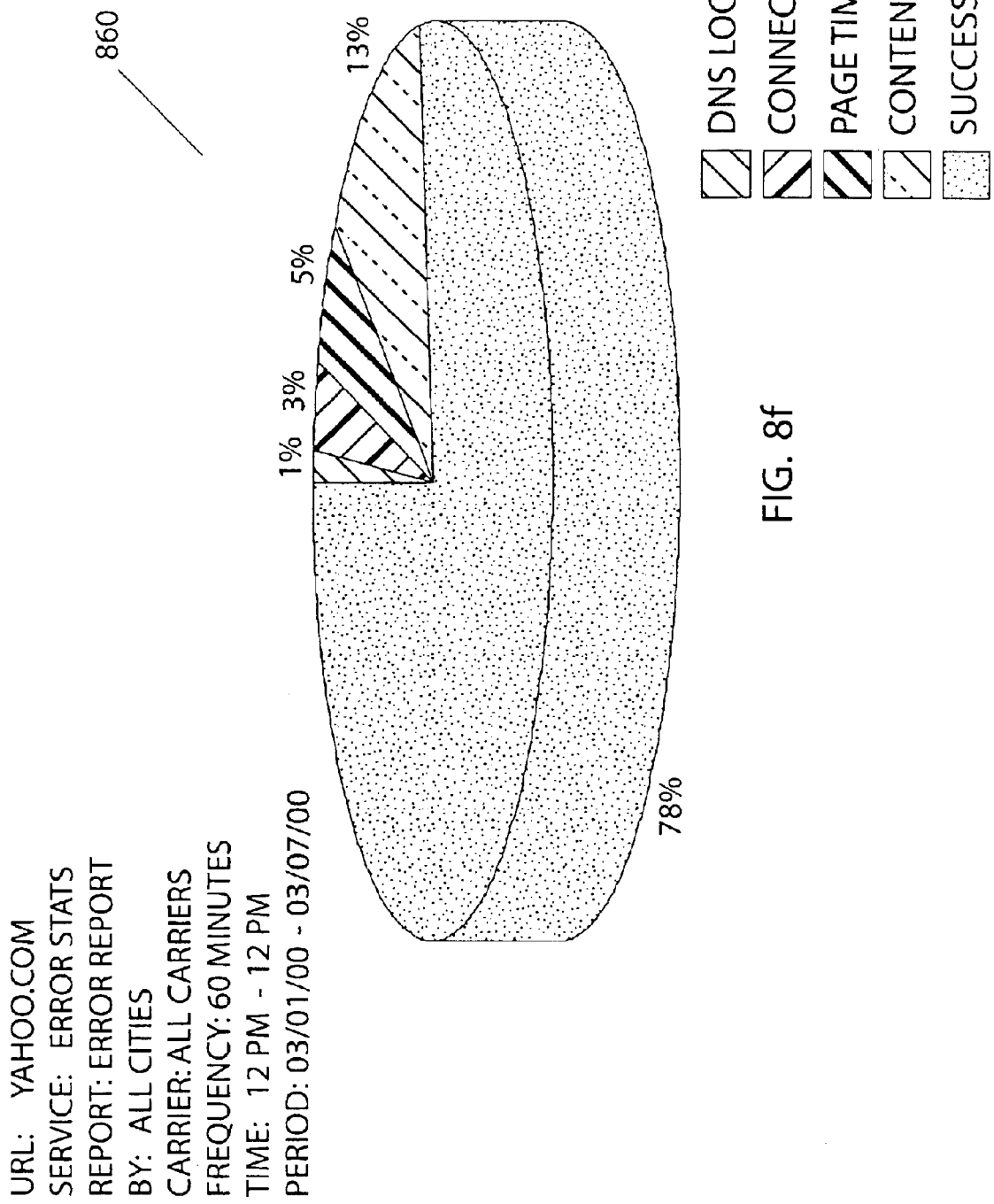

METHOD AND SYSTEM FOR MEASURING DATA QUALITY OF SERVICE IN A WIRELESS NETWORK USING MULTIPLE REMOTE UNITS AND A BACK END PROCESSOR

RELATED APPLICATION

This application claims priority from the provisional patent application No. 60/190,691 by James Xanthos, Mark McDowell, Graham Stead, Joseph Khalil, Dave Helinski, and Joseph Kitchell, filed on Mar. 20, 2000. The provisional patent application is incorporated herein by reference, in its entirety, for all purposes.

BACKGROUND OF THE INVENTION

1. Field of the Invention

The present invention relates generally to a method and system for measuring quality of service in a wireless network.

The present invention relates specifically to a method and system for measuring quality of service in a wireless network using multiple remote units and a back end processor.

2. Description of the Related Art

There are two major technical fields that have shown explosive growth over the past few years: the first is wireless communications and the second is use of data services, particularly the Internet. These two technical fields both require a set of specialized tools in order to measure their quality of service. Interestingly, wireless communications and data services are beginning to converge.

Unfortunately, this convergence has not been accompanied by the development of appropriate specialized tools to measure data quality of service in the wireless network.

The growth of wireless communications has been astounding. Twenty years ago, there was virtually no use of wireless communications devices such as cellular phones. In contrast, the market penetration for wireless devices in the U.S. in 1999 was 32 percent. The current forecast is that 80 percent of the U.S. population will be wireless subscribers by 2008.

There are a variety of specialized tools that are used to measure quality of service over wireless networks. These include the following (just to name a few examples):

Ascom QVoice (including QVoice unattended);
Ericsson TEMS, RSAT-2000, Benchmarker, CellAD, and CeNA;
Nokia TOM;
Safco VoicePrint, DataPrint, and WalkAbout;
Comarco BaseLINE and Gen II;
Grayson Surveyor;
ZK CellTest DX136 and DXC;
Ameritec Swarm;
Neopoint Datalogger; and
Qualcomm QCTest Retriever and QCTest CAIT.

The general deficiency with these tools is that they were primarily developed to measure voice quality and/or RF parameters over the wireless system and not to measure data quality. Some of them have been modified to include some rudimentary data measurements; however, they are not optimized for performing wireless data measurements. In particular, they do not allow unattended measurement of wireless data from multiple remote units in a statistically significant manner with remote control from a back end processor.

The classical way of measuring voice quality of service and/or RF parameters in a wireless network involves sending out technicians to drive test the network. The drive test includes placing the test instrument in a vehicle and running a test script that either generates or receives a voice test signal. The receiving end of the communication link uses a DSP containing a model of human hearing to analyze the received voice sample and produce an associated quality score. In addition, some of the systems measure other system parameters such as SINAD, noise, distortion, received signal level, and call progress statistics.

Unfortunately, the classical method of measuring voice quality of service and/or RF parameters does not function very well for measuring data quality of service. In order to make statistically significant measurements of data quality of service over a wireless network, it is necessary to make multiple measurements from multiple remote devices. Furthermore, a measurement of data quality is inherently different from the other types of measurements due to the effects of latency and other effects that are specific to data.

Most of the existing measurement devices do not have this capability for a variety of reasons. The price of the test instruments range anywhere from $5K to $100K. This makes it price prohibitive to field a statistically significant fleet of remote devices. Thus, what is needed are remote devices designed for unattended operation that is remotely controlled by a back end processor in order to reduce manpower costs. Additionally, what is needed are remote devices that are optimized for performing measurements that are useful over wireless data networks, such as latency for Web page access or delay in SMS message delivery.

The growth of data services has been just as astounding as the growth rate for the wireless industry. The largest driving force behind the growth of data services has been the enormous growth of the Internet. For example, there were 130 Web sites in June 1993, 230,000 Web sites in June of 1996, and 10 million Web sites at the end of 1999.

There have been a variety of specialized tools developed to measure the data quality of service over the Internet.

U.S. Pat. No. 6,006,260 to Barrick, Jr. et al. (assigned to Keynote Systems, Inc) discloses a method for gathering latency experienced by a user over a network. The steps of the method include a user browser sending a GET command to retrieve an HTML page with an embedded Java script. The Java script starts a timer and generates a GET command to retrieve an HTML page. When the page is received, the timer is stopped and the timer information along with cookie data stored on the browser machine is sent to a relay server that logs the information.

U.S. Pat. No. 5,657,450 to Rao et al. teaches the provision of time estimates for long-running distal source access operations using an intermediate server close to the client workspace.

U.S. Pat. No. 5,796,952 to Owen et al. discloses a method for monitoring a user's time of page browsing.

U.S. Pat. No. 6,012,096 to Link et al. teaches a method for monitoring client-to-client network latency for gaming applications. The method involves a ping, response, and response-response protocol.

Unfortunately, none of these patents teach a method which is appropriate for performing data quality of service measurements over a wireless network.

As previously mentioned, there is a tremendous convergence taking place that combines the wireless network with data services. Dataquest estimates that the U.S. wireless data market (including phones, PDAs, laptops, and the like.) will grow from 3 million subscribers in 1999 to 36 million subscribers in 2003. Ericsson is estimating that 1 billion wireless units will be in use worldwide by 2003 and that 40 percent (400 million) of these units will be employed by data users. Furthermore, Ericsson is predicting that 2003 will be the crossover year in which wireless Web access will exceed wired Web access.

As a further measure of the explosive growth of the convergence of the wireless systems and the Internet, one can look at projections for the number of wireless portal subscribers. According to the Strategis Group, the number of wireless portal subscribers will increase from 300,000 in 2000, to 9.8 million in 2003, and finally to 24.8 million in 2006.

A variety of technical advancements have accelerated the convergence of Internet access over wireless devices. In 1997, three competing handset vendors (Nokia, Ericsson, and Motorola) and a small software company (Phone.com, formerly Unwired Planet) joined forces to create a standard way to transmit Internet data to wireless phones without occupying too much bandwidth. The result of this collaboration was development of the wireless application protocol (WAP). One basic component of WAP was development of the WML (Wireless Markup Language, replacing the previous Phone.com Handheld Device Markup Language, HDML) that compresses Web content in comparison to HTML. Additionally, the WAP forum developed standards for the use of microbrowsers in mobile devices.

Unfortunately, the development of wireless Web access technology has significantly outpaced the development of wireless data measurements tools. Accordingly, there is a tremendous need for specific test tools to address the converging technologies of wireless systems and data communications.

SUMMARY OF THE INVENTION

In order to meet this need, a measuring tool is provided for measuring data quality of service over the wireless network. This tool was designed from the ground up with a variety of specific attributes.

The present invention provides for a method and system for measuring data quality of service in a wireless network using multiple peripatetic (i.e. mobile) and/or stationary, unattended, position and performance instruments (PUPPIs) that are remotely controlled by a back end processor. According to some embodiments of the invention, the data service whose quality is measured relates to wireless Internet access, e-commerce transactions, wireless messaging, or push technologies. According to other embodiments of the invention, the system includes an element that is located within the wireless network infrastructure, for example, at the WAP gateway to monitor the wireless data protocol and to perform benchmarking measurements.

The remote unit is able to provide an appropriate statistical distribution for data measurements. The remote units can be peripatetic (i.e. mobile) so that they are able to roam over a statistically significant geographical area, or stationary with pre-planned location at statistically significant points, or some combination of mobile and stationary.

Furthermore, the system includes multiple remote units that are unattended and are remotely controlled by a back end processor. This allows for a large quantity of measurements to be taken in a fully automated manner.

Additionally, each of the remote units provides position information for each measurement as well as performance information that is related to wireless data. More specifically, the performance information may be related to wireless Internet access, e-commerce transactions, or wireless messaging using either push or pull technologies.

For example, one of the most critical measurements for the wireless Internet user is a measurement of the latency, i.e. the amount of time it takes to receive a response after a GET command is sent. In the case of wireless messaging, the latency measurement includes the amount of time required to receive information after it is sent from the source.

In addition, it is useful to perform measurements which divide the network into a wireless and wired portion and that provide separate measurements for each portion. Accordingly, the system may include an element that is located within the wireless network infrastructure, for example at the WAP gateway, to monitor the wireless data protocol and to perform benchmarking measurements.

Accordingly, an object of the present invention is to provide a method and system for measuring data quality of service in a wireless network using multiple remote units and a back end processor.

A further object of the invention is to perform these measurements on a variety of different types of traffic wireless networks, such as iDEN, CDMA, TDMA, and GSM, for example.

Another objective of the invention is to perform these measurements during a variety of different types of communications such as circuit switched calls, packet data calls, SMS messages, wireless internet access, wireless internet transactions (including e-commerce), and during the reception of push data (i.e. data which is delivered using push technology).

A further objective of the invention is to collect a variety of different types of measurements such as latency measurements, reliability (e.g. BER/FER), layer 3 network information, RF information, call connection information, and the like.

Another objective of the invention is to use control links that are either wired or wireless.

A further objective of the invention is to use remote units that are either mobile, stationary, or some combination of mobile and stationary so that they provide statistically significant measurements.

Another object of the invention is to provide a back end which allows user access through the Internet, allows for post-processing of the received data, allows for scheduling collection missions based on available resources, and allows for generation of test traffic.

An additional object of the invention is to provide a remote unit that allows for storage and pre-processing of the measured data, battery backup, and an RF scanner.

Advantages of the current invention include the ability to collect statistically significant data in an extremely cost effective and easy to use manner.

BRIEF DESCRIPTION OF THE DRAWINGS

FIG. 1a shows the communication path for the traffic data in a standard wired Internet measurement system.

FIG. 1b shows the communication path for the traffic data during a circuit switched data connection in accordance with an embodiment of the invention.

FIG. 1c shows the communication path for the traffic data during a packet switched data connection in accordance with an embodiment of the invention.

FIG. 1d shows the communication path for the traffic data during an SMS message transmission in accordance with an embodiment of the invention.

FIG. 1e shows the communication path for the traffic data during a WAP data connection in accordance with an embodiment of the invention.

FIG. 1f shows the communication path for the traffic data during a WAP data connection in accordance with a further embodiment of the invention.

FIG. 1g shows the communication path for the traffic data during a WAP data connection, including a WAP monitoring processor, in accordance with a further embodiment of the invention.

FIG. 3a shows the basic architecture for the remote unit in accordance with one embodiment of the invention.

FIG. 3b shows another architecture for the remote unit with separate control link modem and traffic modem according to an alternate embodiment of the invention.

FIG. 3c shows another architecture for the remote unit with separate control link modem and multiple traffic modems according to another alternate embodiment of the invention.

FIG. 3d shows a further architecture for the remote units that include multiple peripherals in accordance with one embodiment of the invention.

FIG. 4a shows a hardware implementation of the remote unit using either a laptop or handheld unit in accordance with one embodiment of the invention.

FIG. 4b shows a hardware implementation of the remote units using a single board computer (SBC) in accordance with one embodiment of the invention.

FIG. 4c shows the organization of the software-defined radio in accordance with an embodiment of the invention.

FIG. 4d shows the organization of the software in the remote unit in accordance with an embodiment of the invention.

FIG. 8b shows a bar graph output of download times across different wireless networks in accordance with an embodiment of the invention.

FIG. 8f shows a pie chart of error statistics for wireless access of Yahoo in accordance with an embodiment of the invention.

DETAILED DESCRIPTION OF THE INVENTION

Overview

In order to understand the present invention, it is helpful to compare the communication path of current data measurements tools with the communication path in accordance with several embodiments of the invention. FIGS. 1a–g show a generic communication network with a variety of wireless communication paths connected to the Internet. It is well known to those of ordinary skill in the art that these figures illustrate a generic network that is used for illustrative purposes. For example, in some cellular networks there is a base station controller connected to multiple base stations between their connections to the MSC. As another example, the WAP gateway, packet data gateway, and PSTN connection may be replaced in some wireless networks by a single device that is directly connected to the MSC.

Figure 1A:
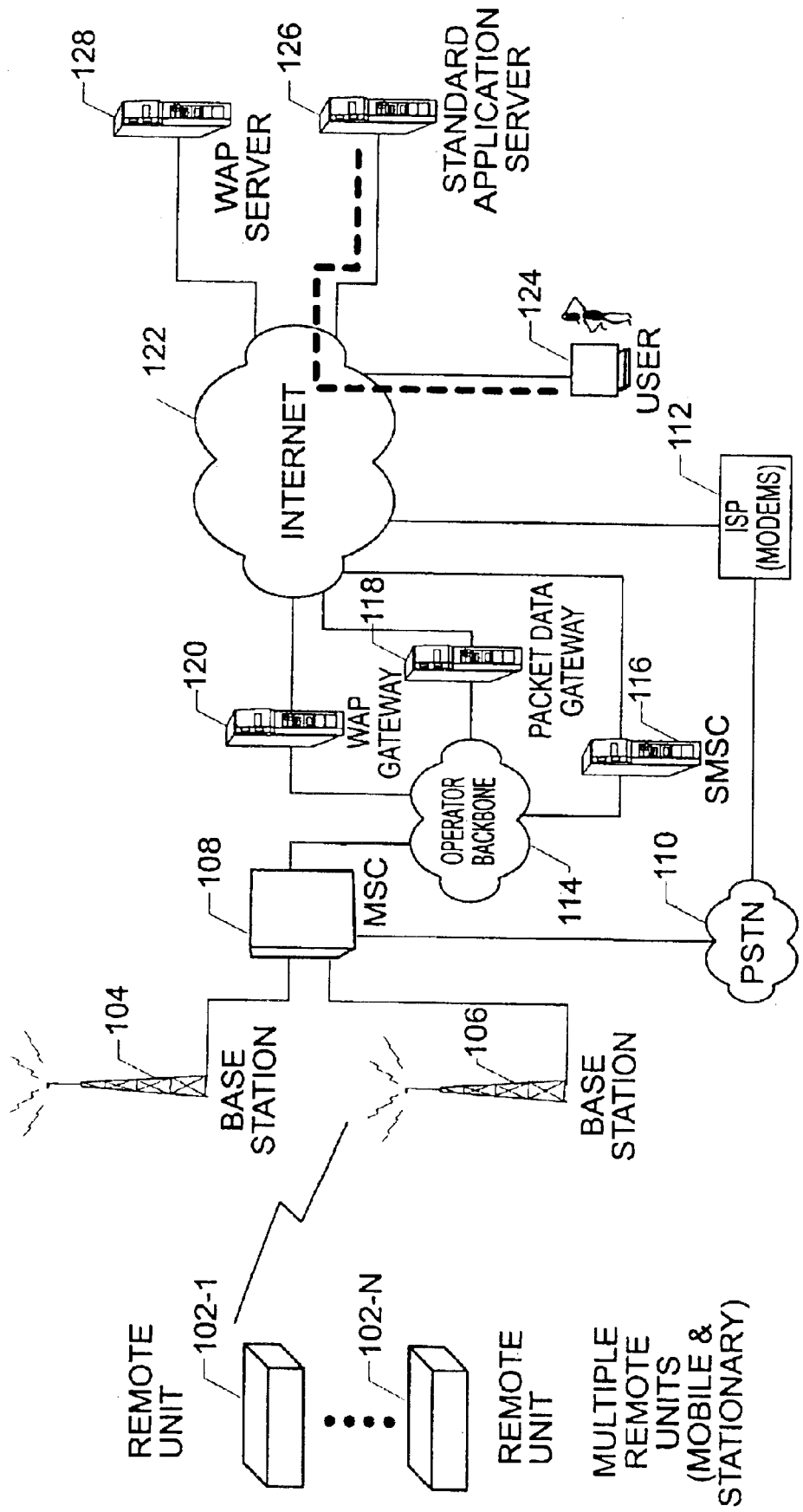
FIGS. 1a–g show a generic communication network with a variety of wireless communication paths connected to the Internet

FIG. 1a shows the communication path (heavy broken line) for the traffic data in a standard wired Internet measurement system. The traffic data flows between the user machine 124 over the Internet 122 to a standard application server 126 that will generally be serving an HTML page.

Figure 1B:
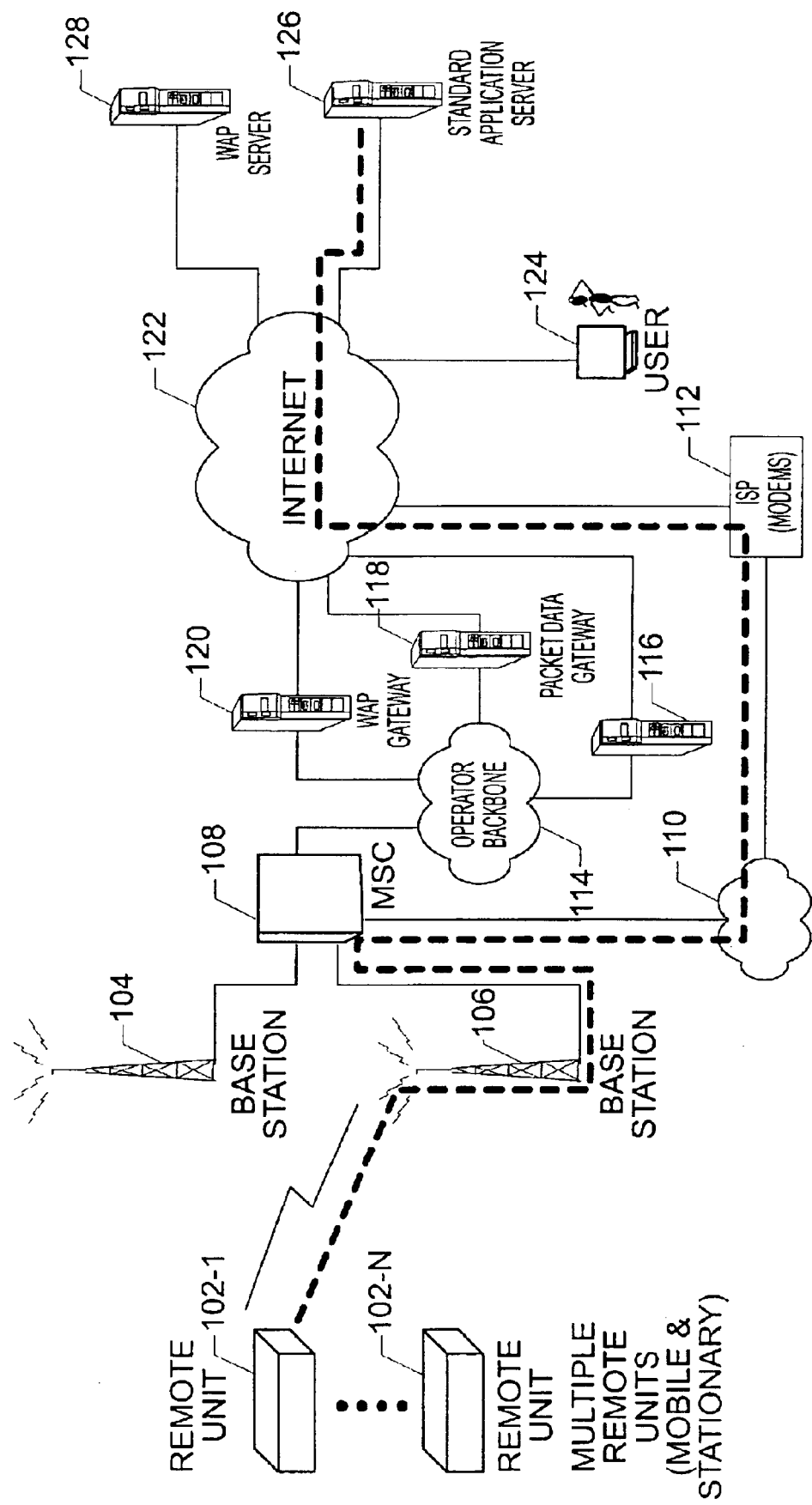

FIG. 1b shows the communication path (heavy broken line) for the traffic data during a circuit switched data connection in accordance with an embodiment of the invention. The traffic data passes from the remote unit 102-1 to the base station 106, MSC 108, PSTN 110, ISP 112, Internet 122, and to a standard application server 126. The standard application server 126 may be serving an HTML page, for example.

Figure 1C:
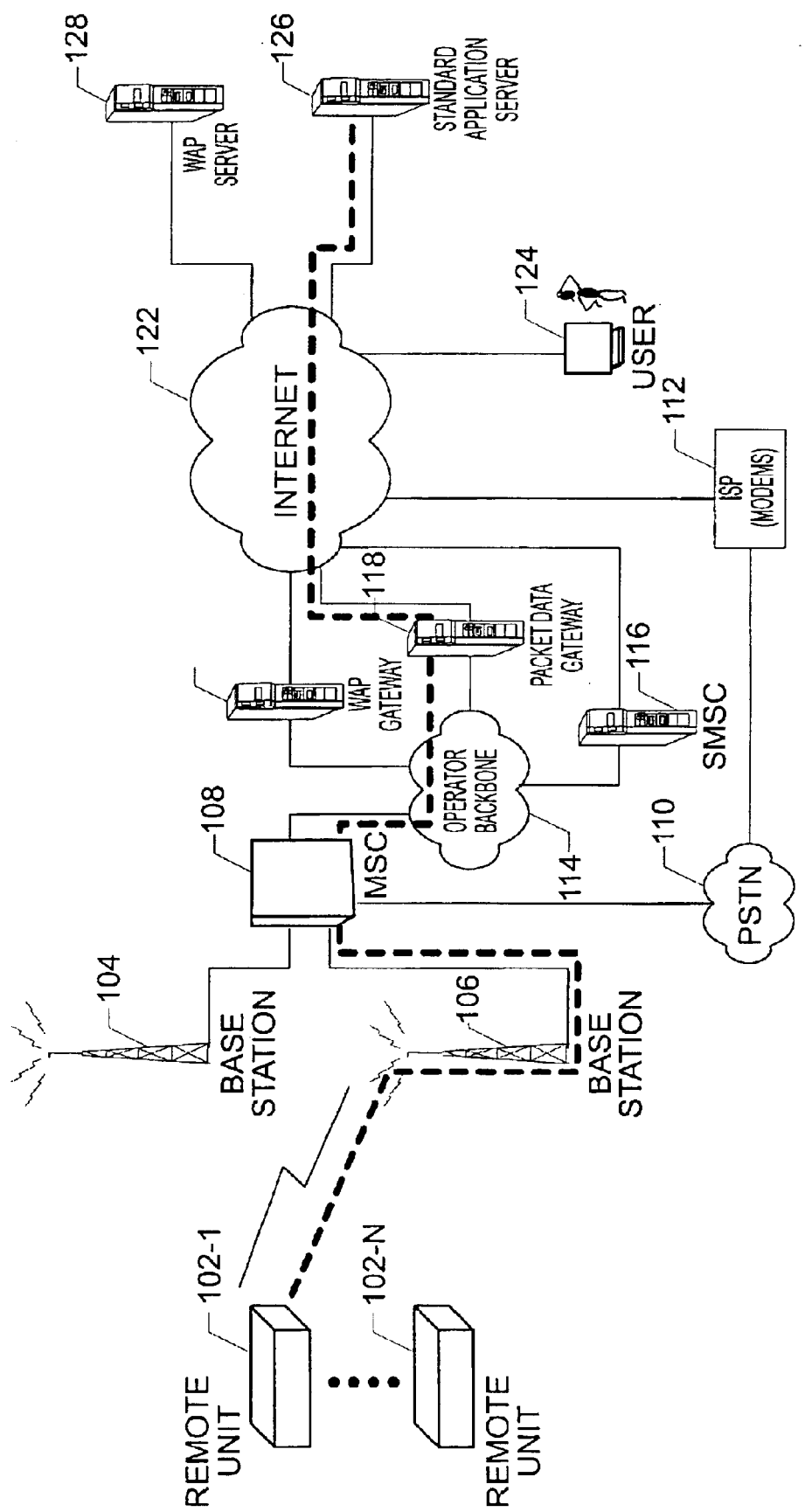

FIG. 1c shows the communication path (heavy broken line) for the traffic data during a packet switched data connection in accordance with an embodiment of the invention. The traffic data passes from the remote unit 102-1 to the base station 106, MSC 108, operator backbone 114, packet data gateway 118, Internet 122, and standard application server 126. For example, the standard application server 126 may be serving an HTML page.

Figure 1D:
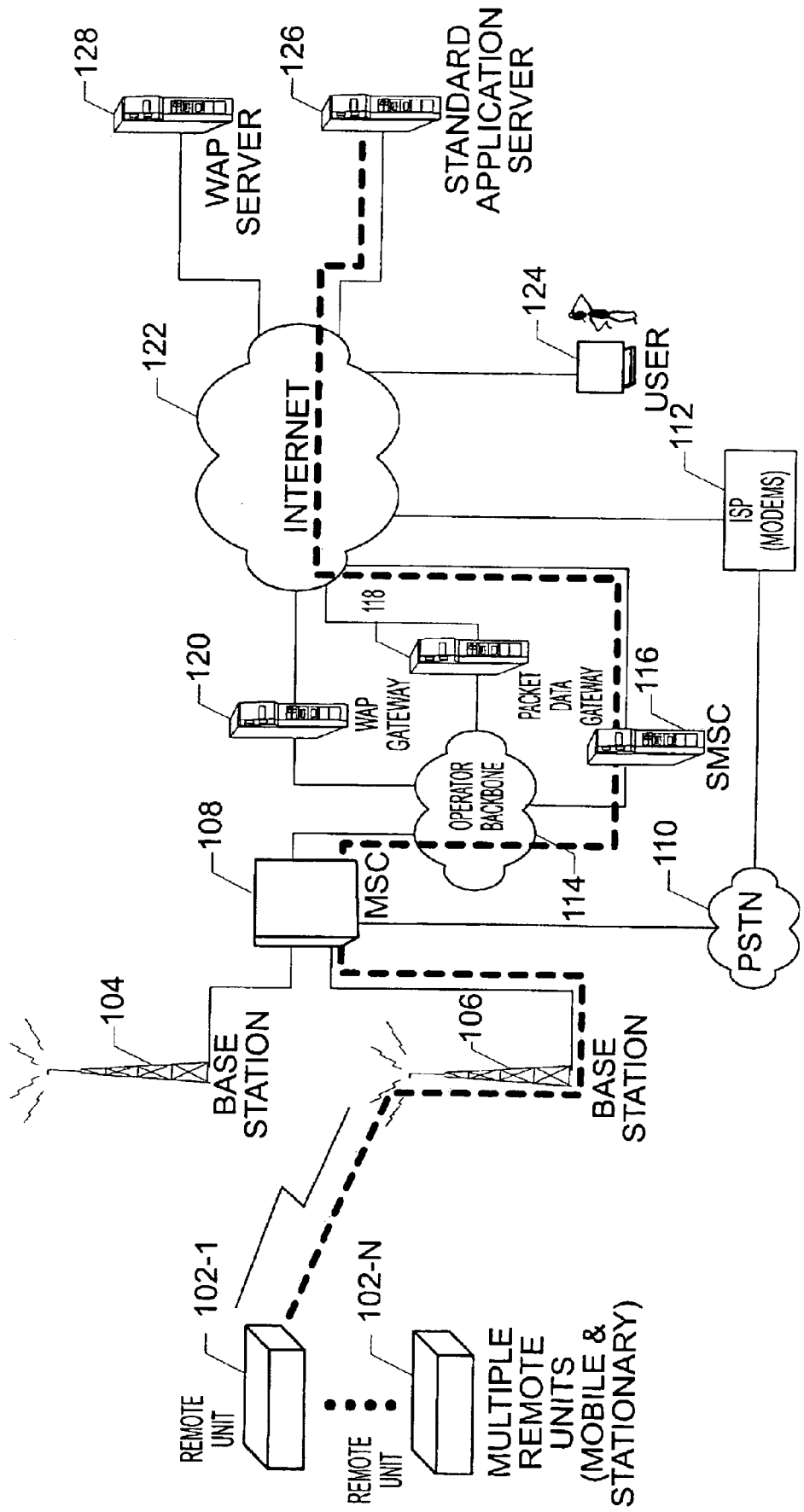

FIG. 1d shows the communication path (heavy broken line) for the traffic data during an SMS message transmission in accordance with an embodiment of the invention. If the SMS message is being delivered to the remote unit 102-1, the traffic data passes from a standard application server 126 to the Internet 122, SMSC 116, operator backbone 114, MSC 108, base station 106, and remote unit 102-1.

Figure 1E:
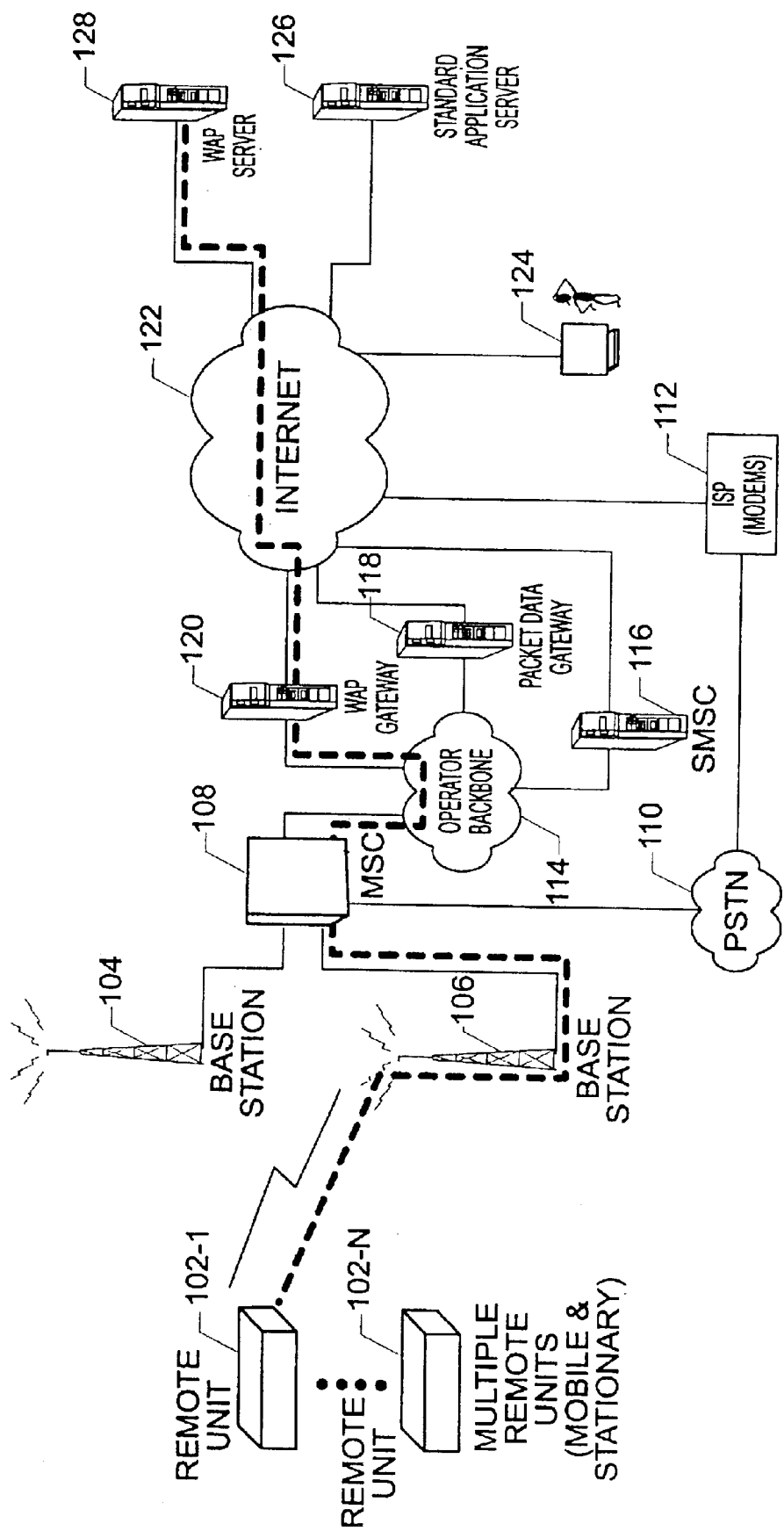

FIG. 1e shows the communication path (heavy broken line) for the traffic data during a WAP data connection in accordance with an embodiment of the invention. If the remote unit 102-1 is accessing a WAP server 128, the traffic data passes from the remote unit 102-1 to a base station 106, MSC 108, operator backbone 114, WAP gateway 120, Internet 122, and WAP server 128. For example, the traffic data path shown in FIG. 1e allows for latency measurements for wireless Web page access or e-commerce transactions.

It is important to note that the term WAP is being used generically to refer to any wireless Internet protocol, including HDML and any future wireless Internet protocols that may be developed. The following examples are provided of some competing technologies that for the purposes of this patent will be referred to generically as WAP. For example, the Web content can be delivered as text messaging or as an SMS message (as proposed by Xypoint or GoSMS) so that it is compatible with existing cellular phones. Alternatively, the Web content can be delivered as existing HTML Internet content for wireless devices as proposed by Spyglass' Prism technology or Japan's iMode. As a further example, the content can be processed through a template model that reads existing HTML content and fits the data to a template optimized for various types of wireless phones such as the system proposed by Everypath.com. As another example, the data content can be delivered to a Palm Pilot or other PDA or handheld device that uses a proprietary protocol.

Figure 1F:
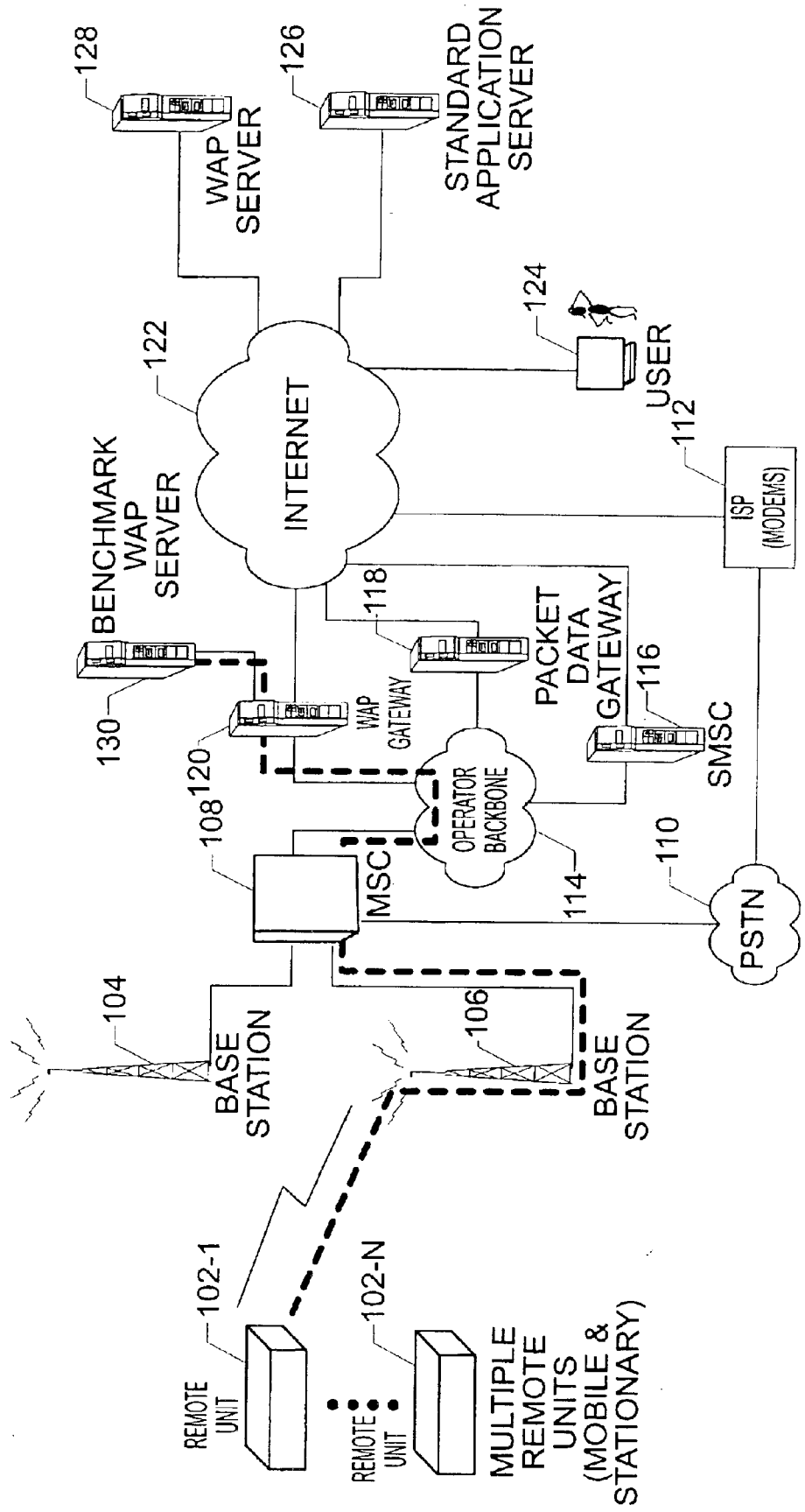

FIG. 1f shows the communication path (heavy broken line) for the traffic data during a WAP data connection in accordance with a further embodiment of the invention. If the remote unit 102-1 is accessing the benchmark WAP server 130, the traffic data passes from the remote units 102-1 to a base station 106, MSC 108, operator backbone 114, WAP gateway 120, and to the benchmark WAP server 130. This configuration allows latency measurements without including the uncertainties of the latency through the Internet 122 itself. In other words, the configuration in FIG. 1f allows measurements of the latency due to the wireless network itself with no contribution from the Internet 122.

Figure 1G:
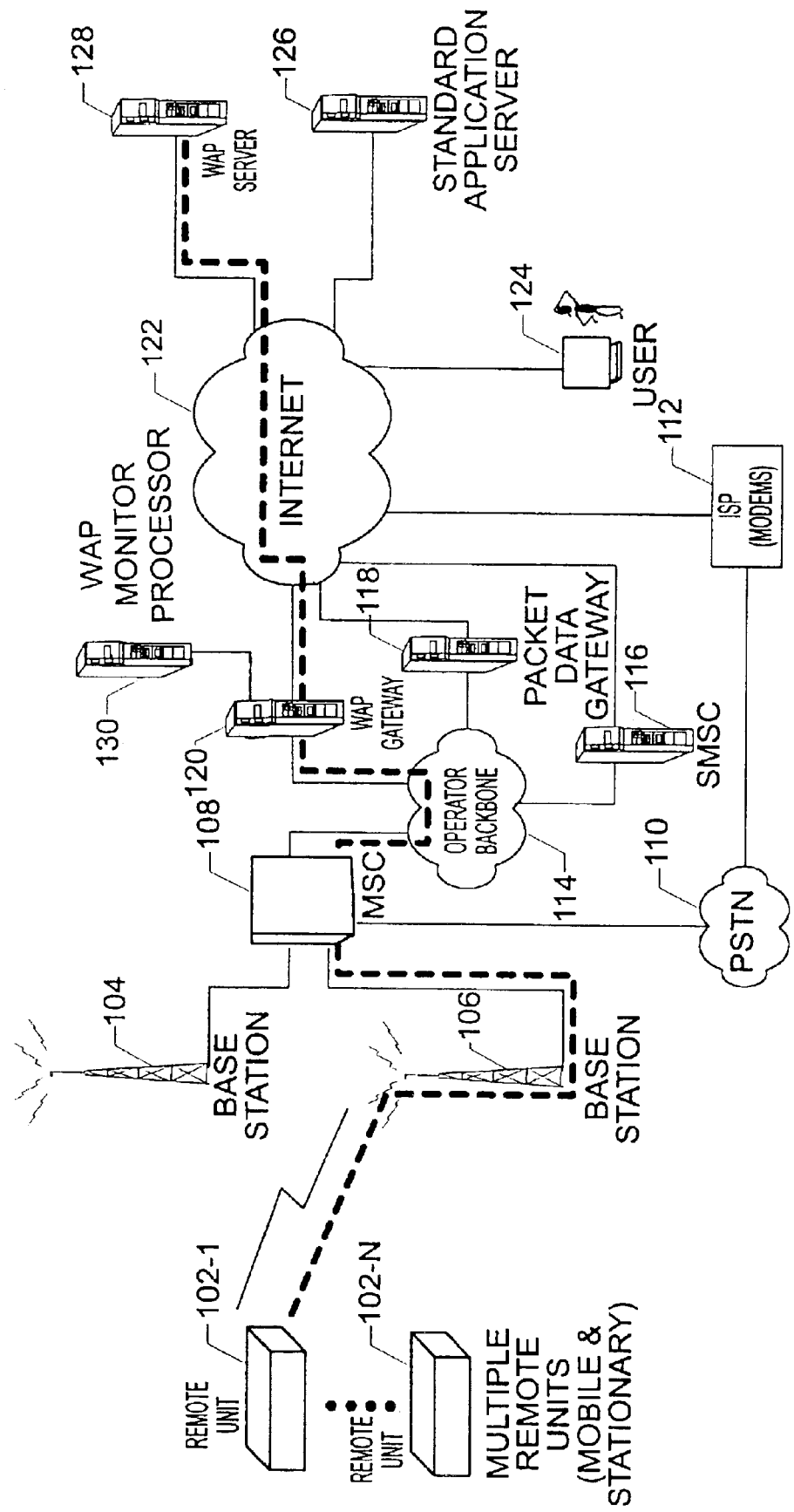

FIG. 1g shows the communication path (heavy broken line) for the traffic data during a WAP data connection, including a WAP monitoring processor 132, in accordance with a further embodiment of the invention. The WAP monitoring processor 132 may be implemented as monitoring software installed and running on the WAP Gateway 120 or as software installed on a separate machine attached to the WAP Gateway 120. The software would monitor traffic through the WAP Gateway 120 and provide metrics such as throughput, latency and lost packet information. This configuration would allow the wireless network and the Internet 122 itself to be analyzed and monitored separately, thus providing performance information for each. Furthermore, the WAP Monitoring Processor 132 would be able to collect protocol information directly from the WAP Gateway 120 that may not be available to the multiple remote units (102-1 through 102-N).

The monitoring software may run as a separate application on the WAP Gateway 120, or may be embedded into the WAP Gateway software itself and run as part of the entire gateway application. The monitoring software would have a mechanism for collecting metrics and passing that information to the back end processor through the internet, wireless network, or through some other means.

The monitoring software may temporarily store results locally, and perform some pre-processing on the data prior to forwarding it to the back end processor.

Figure 1H:
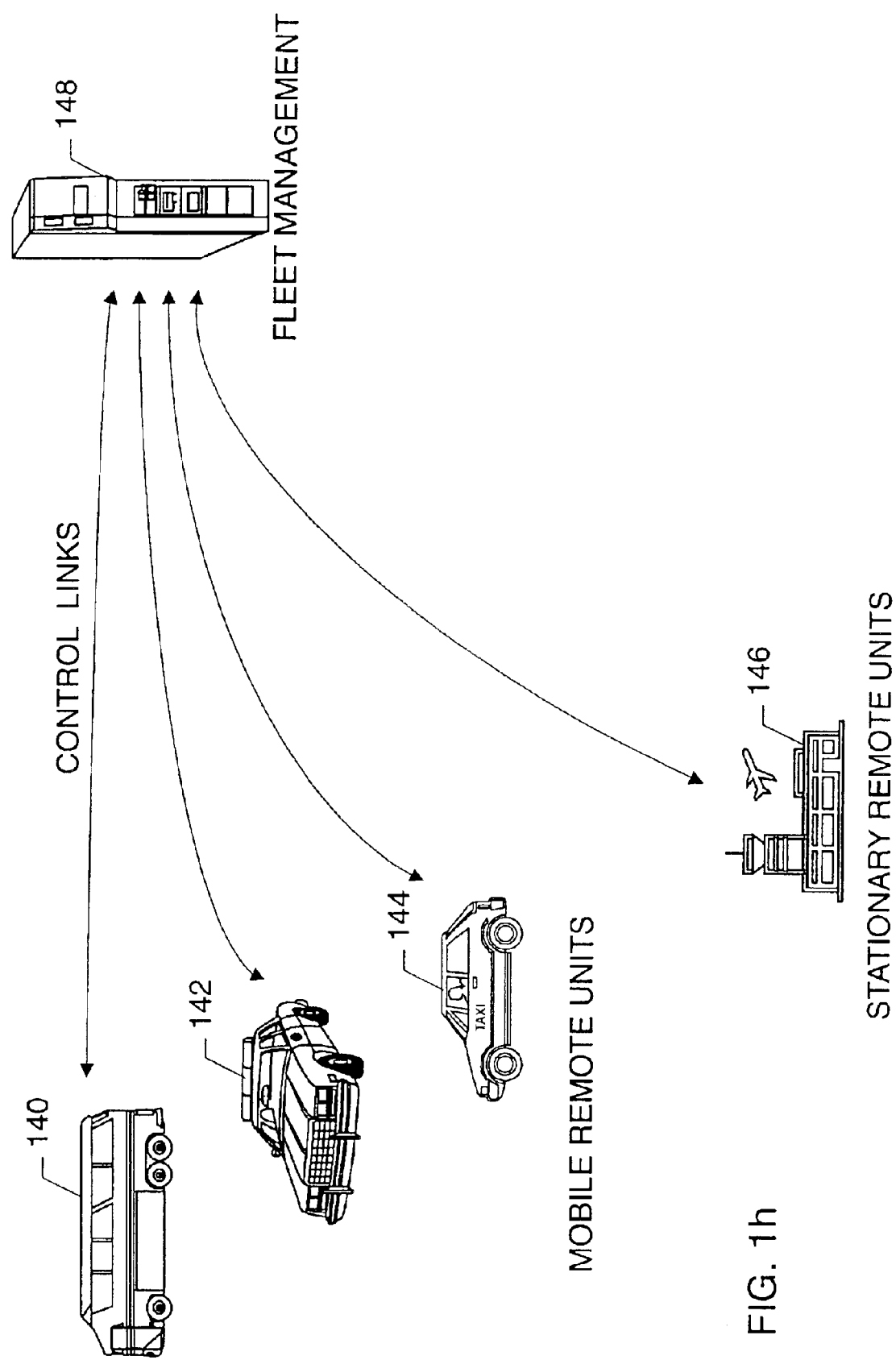
FIG. 1h shows the communication path for the control link in accordance with an embodiment of the invention.

FIG. 1h shows the communication path for the control link in accordance with an embodiment of the invention. The control link is used to remotely control the remote units 140, 142, 144, 146 from the back end processor 148. Specifically, the process in the back end processor 148 that communicates with the remote units 140, 142, 144, 146 is the fleet management process, which will be discussed in detail later.

The remote units can be either mobile 140, 142, 144 or stationary 146. The mobile units 140, 142, 144 can be mounted in a variety of vehicles such as taxis, police cars, buses, postal vehicles, delivery vehicles, fleet vehicles, just to give a few examples. The stationary remote units 146 can be mounted in any area in which the public congregates and uses wireless devices. This includes airports, bus stations, and train stations just to provide a few examples.

A variety of communication technologies are available to implement the control link. The control link can be implemented as data running over any of the current wireless networks such as CDMA, iDEN, TDMA, or GSM just to name a few examples. Additionally, the control link can be implemented over the AMPS network using CDPD for example. Alternatively, the control link can be implemented using a two-way data system such as ARDIS, MOBITEX, SKYTEL, and the like.

System Architecture

Figure 2A:
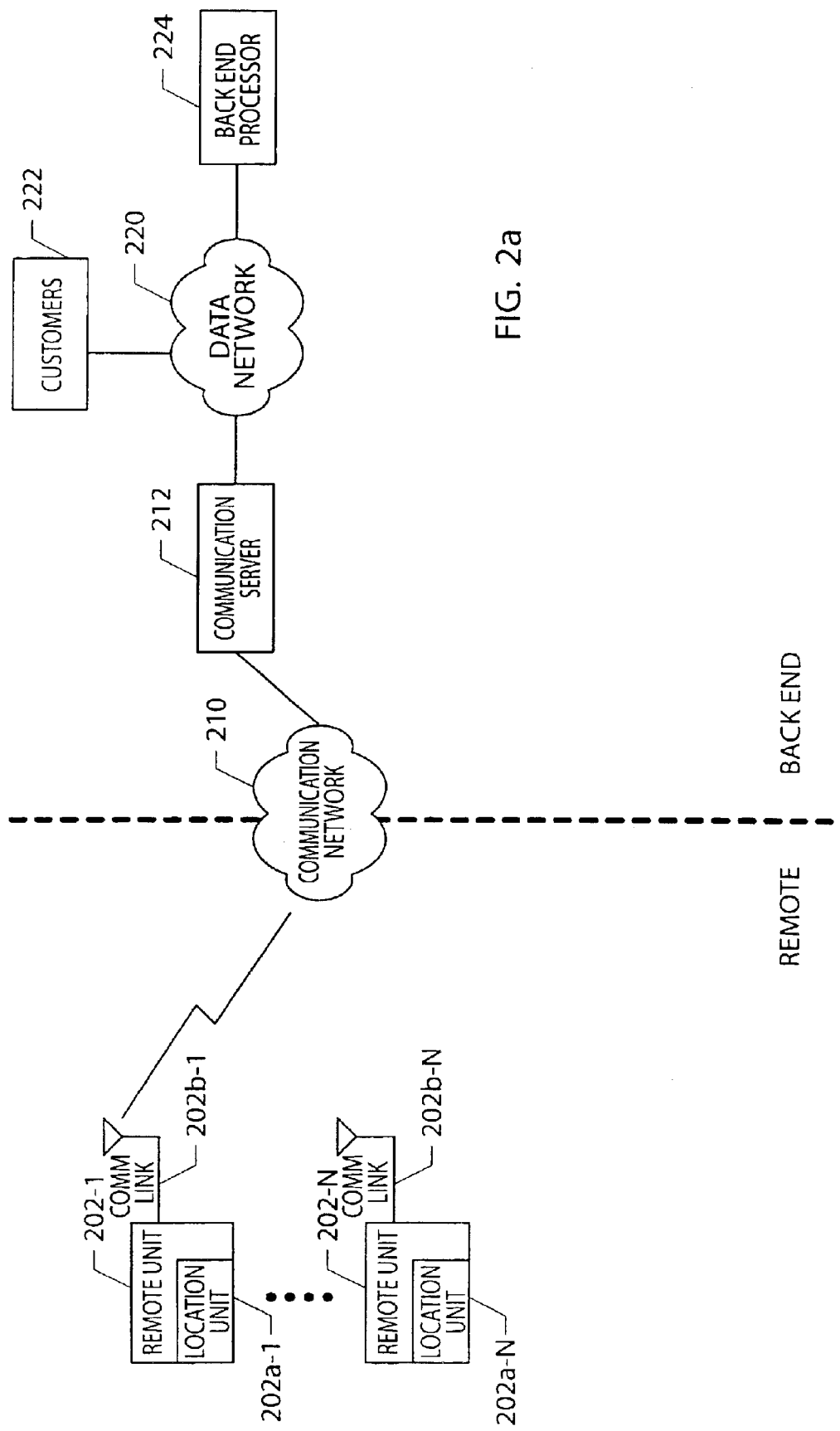
FIG. 2a shows the system architecture in accordance with one embodiment of the invention.

FIG. 2a shows the system architecture in accordance with one embodiment of the invention. As previously described, the invention comprises multiple remote units (202-1–202-N) that may be either mobile or stationary. Each remote unit may include a location unit (202a-1–202a-N) that allows the remote unit to accurately determine its location. Furthermore, each remote unit includes a communications link (202b-1–202b-N) that provides for both the control link and the traffic data. The communications link 202b-1 communicates over a communication network 210 that passes the information to a communication server 212 that connects to a data network 220. The data network 220 can be a public data network, such as the Internet, or a private data network. A back end processor 224 is connected to the data network 220 for handling control link information, both commands and responses, and traffic data. In addition, the customers 222 are also connected to the data network so that they can access the back end processor 224.

Figure 2B:
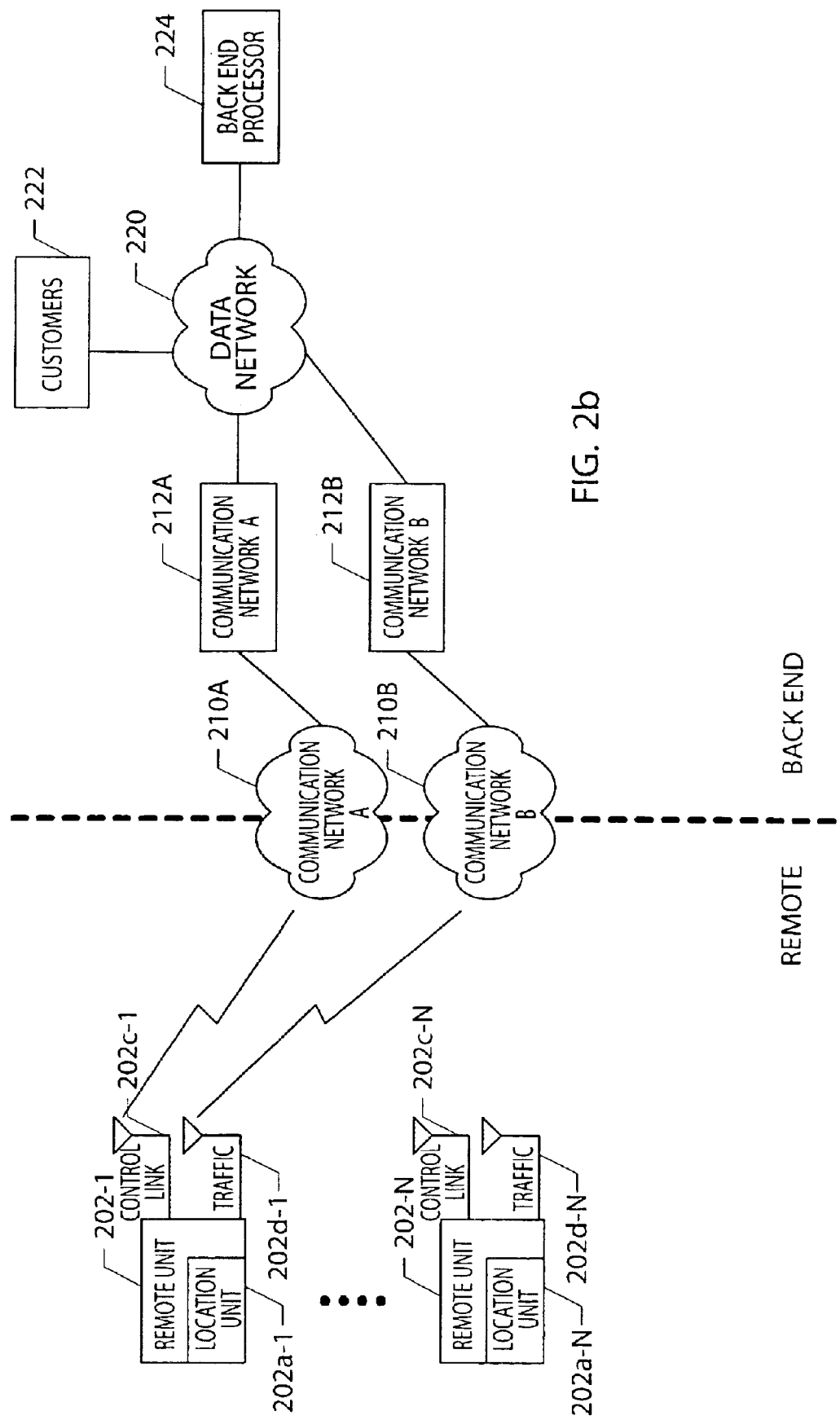
FIG. 2b shows the system architecture in accordance with a further embodiment of the invention.

FIG. 2b shows the system architecture in accordance with a further embodiment of the invention. The system in FIG. 2b differs from the system shown in FIG. 2a in that the control link network and the traffic data network are two separate communication networks. Each remote unit (e.g., 202-1) may include a location unit 202a-1 that allows the remote unit 202-1 to accurately determine its location. Furthermore, each remote unit 202-1 includes a control link communication module 202c-1 and a traffic data communication module 202d-1. The control link 202c-1 passes commands and response information through communication network A 210A and communication server A 212A to the data network 220. The traffic data communication module 202*d*-1 passes traffic data through communication network B (210B) and communications server B (212B) to the data network 220. A back end processor 224 is connected to the data network 220 for handling control link information, both commands and responses, and traffic data. In addition, the customers 222 are also connected to the data network 220 so that they can access the back end processor 224.

Figure 2C:
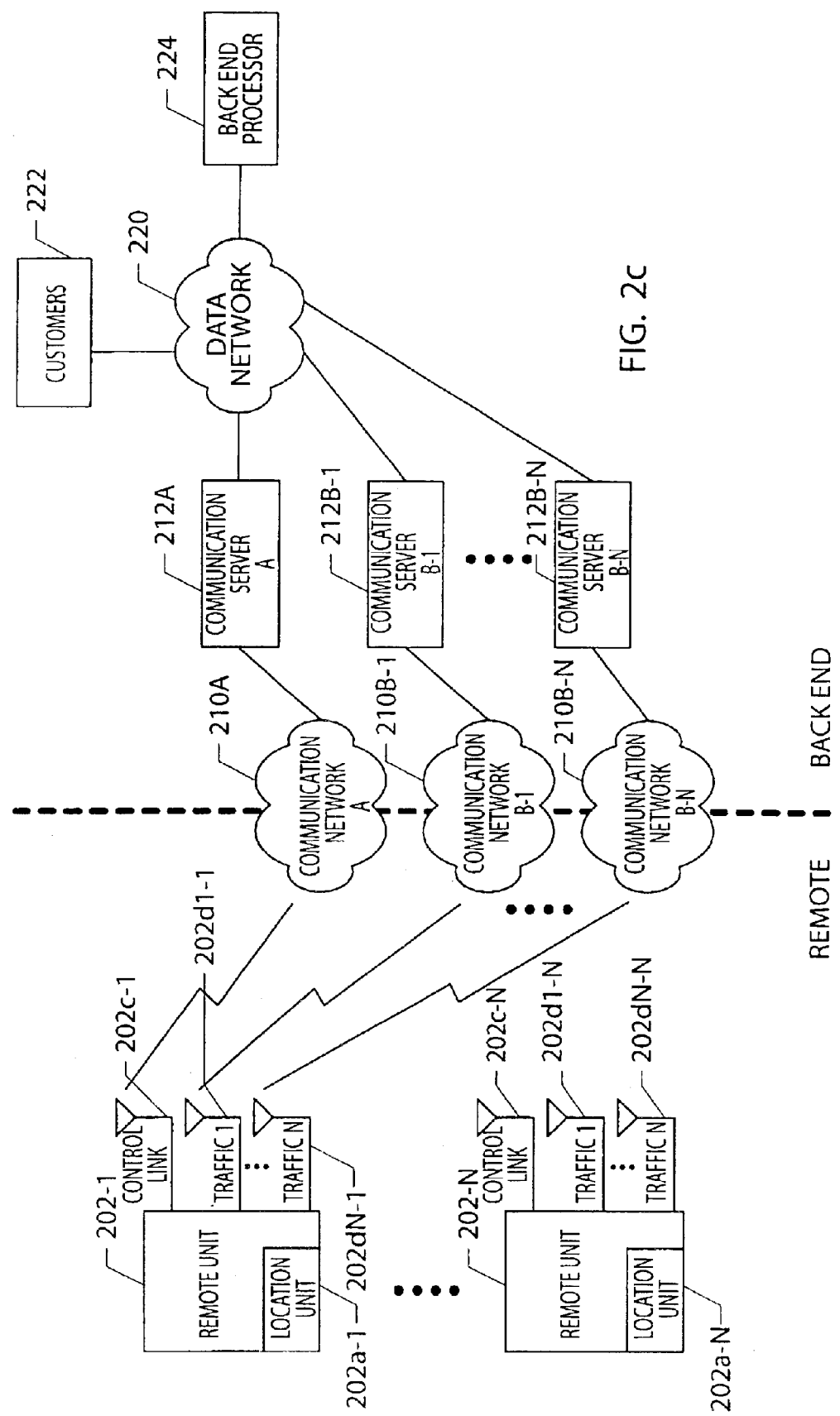
FIG. 2c shows the system architecture in accordance with another embodiment of the invention.

FIG. 2*c* shows the system architecture in accordance with another embodiment of the invention. The system shown in FIG. 2*c* differs from the system shown in FIG. 2*b* in that each remote unit (e.g., 202-1) may have multiple traffic modules (202*d*1–202*d*N-1). Each remote unit 202-1 may include a location unit 202*a*-1 that allows the remote unit to accurately determine its location. Additionally, each remote unit 202-1 includes a control link communication module 202*c*-1 and includes multiple traffic data communication modules (202*d*1-1–202*d*N-1). The control link passes command and response information through communication network A 210A and communication server A 212A to the data network 220. Each traffic data communication module 1 through N (202*d*1-1–202*d*N-1) passes traffic data through communication network B-1 (210B-1) through B-N (210B-N), respectively, and through communication servers B-1 (212B-1) through B-N (212B-N), respectively, to the data network 220. A back end processor 224 is connected to be data network 220 for handling control link information, both commands and responses, and traffic data. In addition, the customers 222 are also connected to the data network 220 so that they can access the back end processor 224.

Figure 2D:
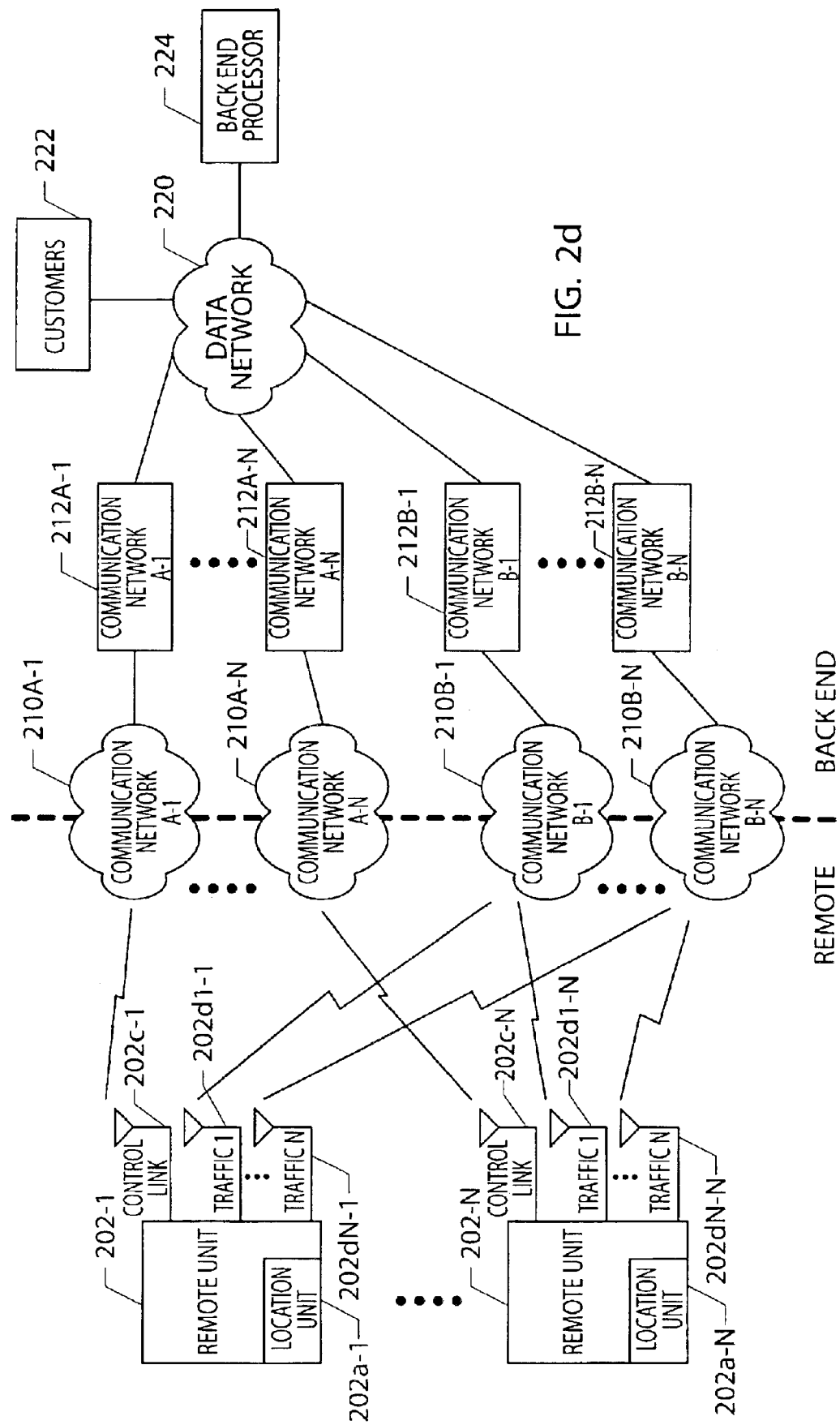
FIG. 2d shows the system architecture in accordance with a further embodiment of the invention.

FIG. 2*d* shows the system architecture in accordance with a further embodiment of the invention. The system in FIG. 2*d* differs from the system shown in FIG. 2*c* in that multiple control link communication networks may be used. This is particularly important in systems in which the remote units are deployed in different cities. It may be preferable in this case to use a different control link communication network in different cities depending on the wireless system coverage and the data pricing structure.

Each remote unit (202-1–202-N) may include a location unit (202*a*-1–202*a*-N) that allows the remote unit to accurately determine its location. Furthermore, each remote unit (202-1–202-N) includes a control link communication module (202*c*-1–202*c*-N) and includes multiple traffic data communication modules (202*d*1-1–202*d*N-1–202*d*1-N–202*d*N-N). The control link passes commands and response information through one of communication network A-1 (210A-1) through A-N (210A-N) depending on the appropriate communication network for the specific remote unit. Each control link communication network A-1 (210A-1) through A-N (210A-N) is connected to a respective communication server A-1 (212A-1) through A-N (212A-N) which allows command and response information to be passed to the data network. Each traffic data communication module 1 (202*d*1-1) through N (202*d*1-N) passes traffic data through communication network B-1 (210B-1) through B-N (210B-N), respectively, and through communication servers B-1 (212B-1) through B-N (212B-N), respectively, to the data network. A back end processor 224 is connected to the data network 220 for handling control link information, both commands and responses, and traffic data. In addition, the customers 222 are also connected to the data network 220 so that they can access the back end processor 224.

Figure 2E:
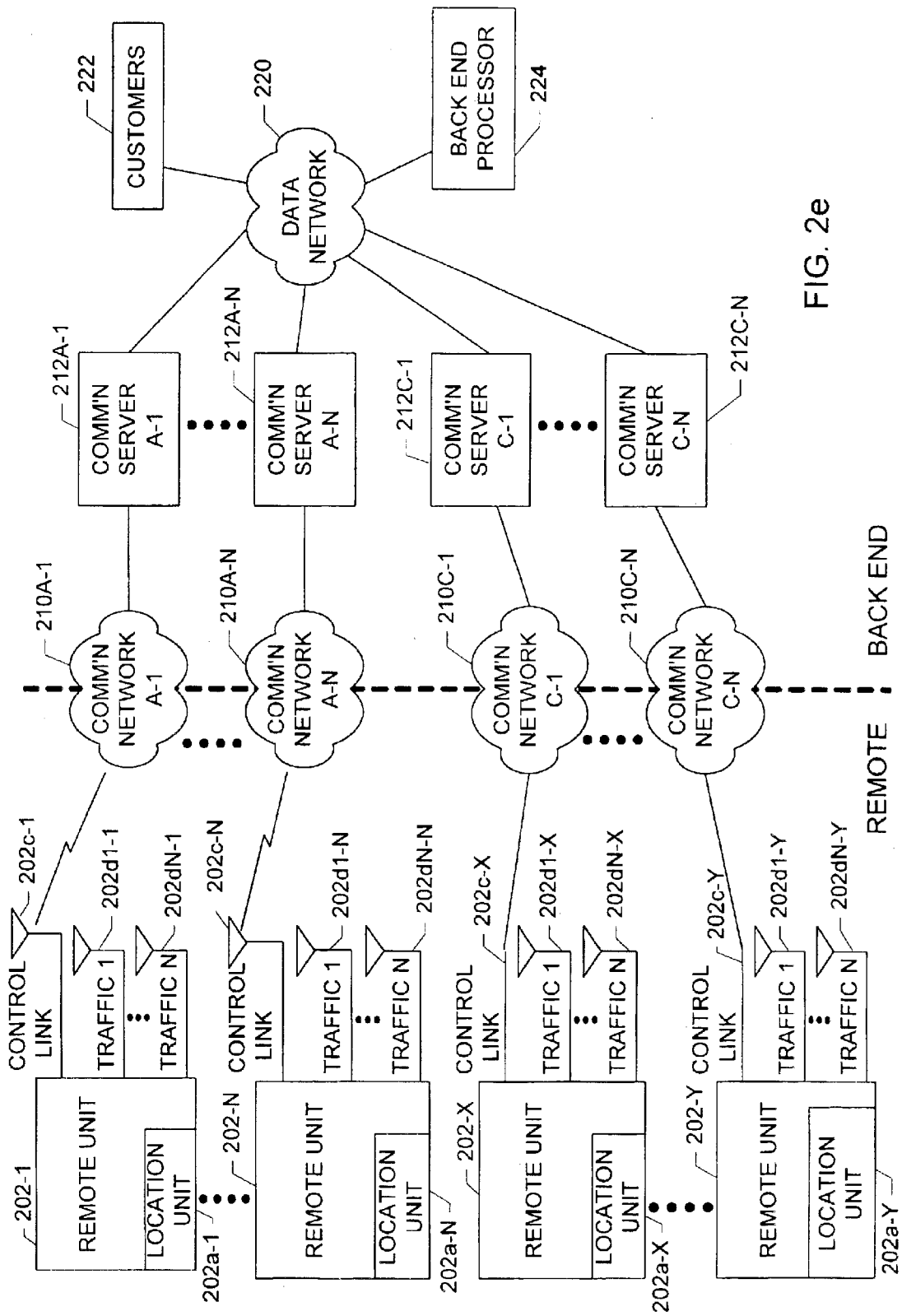
FIG. 2e shows the system architecture in accordance with another embodiment of the invention.

FIG. 2*e* shows the system architecture in accordance with another embodiment of the invention. The system in FIG. 2*e* differs from the system shown in FIG. 2*d* in that both mobile and stationary remote units are shown. Because the traffic data communication channels in FIG. 2*e* are the same as those in FIG. 2*d*, they have been omitted in order to simplify the diagram. The control links for the mobile remote units (202-1 through 202-N) are the same as those described in FIG. 2*d*.

Each stationary remote unit (202-X through 202-Y) may include a location unit (202*a*-X through 202*a*-Y) that allows the remote unit to accurately determine its location. The location unit (202*a*-X through 202*a*-Y) is generally optional in the stationary remote units since their location is presumably known. The stationary remote units each include a control link module (202*c*-X through 202*c*-Y) which is connected via a respective wired line to a respective communication network C-1 (210C-1) through C-N (210C-N) and associated communication server C-1 (212C-1) through C-N (212C-N) which allows command and response information to be passed to the data network 220. A back end processor 224 is connected to be data network 220 for handling control link information, both commands and responses, and traffic data. In addition, the customers 222 are also connected to the data network 220 so that they can access the back end processor 224.

Remote Unit

The remote unit has a variety of attributes in accordance with one embodiment of the invention. The remote unit should preferably be portable in terms of size and is weight so it can be deployed in a vehicle or in a stationary public area. Possible vehicles include buses, police vehicles, taxis, postal vehicles, delivery vehicles, and fleet vehicles just to name a few. Examples of stationary public areas include airports, train stations, bus stations, and any public area where large numbers of people use wireless devices.

Another attribute of the remote unit is that it is mountable either in a vehicle or in a public area. There are a variety of methods that can be used for mounting the remote unit. For example, the remote units can be mounted to a DIN bar that is commonly used for industrial equipment. Alternatively, the remote units can be mounted using a standard bracket, tie device, fabric strap, bolts, or adhesive device such as Velcro, for example.

A further attribute of the remote unit is that it is able to withstand a wide temperature range such as the industrial temperature range of −40 degrees C. to +80 degrees C., for example. This attribute allows deployment of the remote unit in a wide range of geographical environments. Furthermore, it allows deployment of the remote unit in places such as the trunk of a vehicle in which airflow is limited.

Another attribute of the remote unit is the ability to withstand vibration. This attribute is important since many of the remote units may be deployed in vehicles and will be subjected to severe vibration. There are a variety of standard techniques that can be used to improve the vibration performance of the remote unit. These include using frequency absorbing mounting materials and potting the components on the printed circuit board for added stability.

A further attribute of the remote unit is that it meets all local standards for emissions, both radiated and conductive. For example in United States, the emissions from most digital devices are covered by FCC part 15 and emissions from cellular devices are covered by FCC part 22. In Europe, there generally are directives which cover radiated emissions, conductive emissions, and radiated immunity and which must be met in order to receive the CE mark.

Another attribute of the remote unit is the ability to handle the input power source. First, the remote unit should include some type of power regulation. This is particularly important in a vehicular environment in which the power provided by the vehicle battery is very noisy. Additionally, the remote unit should include the ability to power any external modules or peripherals that are going to be attached to the main control unit. Furthermore, the remote units may include some form of battery backup with an automatic charger so that the remote unit in a mobile environment does not drain the vehicle battery when the ignition is turned off. This requirement is not as important in a stationary deployment since the power can be provided from an AC outlet using a DC transformer. However, one may choose to include the battery and charger in this configuration also in order to provide battery backup in the event of an AC power failure. Finally, the remote unit may include some form of sleep mode which is used to conserve power during periods of sporadic activity.

The remote unit will now be described with regard to a variety of embodiments in accordance with the invention. FIGS. 3a through 3d show a variety of basic architectures for the remote unit. FIGS. 4a through 4d show a variety of possible implementations for the remote unit.

Figure 3A:
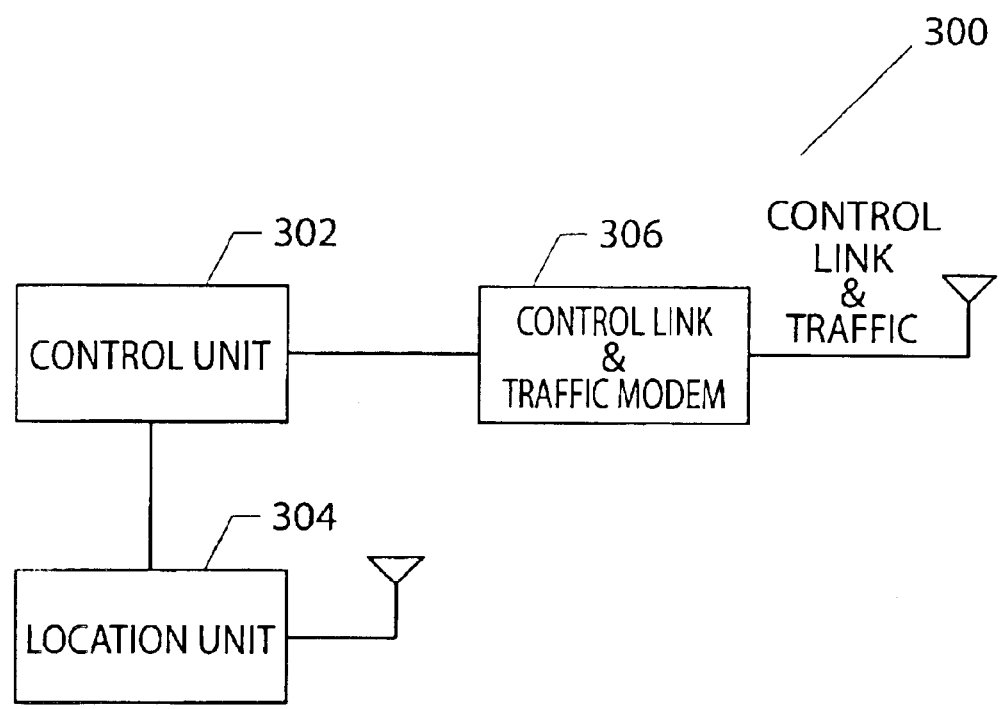
FIGS. 3a through 3d show a variety of basic architectures for remote units according to various embodiments of the invention.

FIG. 3a shows the basic architecture for the remote unit in accordance with one embodiment of the invention. The remote unit 300 comprises a control unit 302, a location unit 304, and a control link and traffic modem 306. The control unit 302 is the main control device for the remote unit 300 and is connected to the location unit 304 and the control link and traffic modem 306. The location unit 304 determines the location of the remote unit 300.

The control link and traffic modem 306 shown in FIG. 3a is used to communicate with the back end processor 224. The control link and traffic modem 306 is connected to the control unit 302 in order to send and receive control information and traffic information. The control unit is generally running a main program that controls the location unit 304 and the control link and traffic modem 306.

There are a variety of ways in which the location unit 304 can determine the location in accordance with the invention. The location unit 304 may comprise a GPS receiver such as those manufactured by Trimble, Ashtech, Garmin, or Magellan, for example. If the location unit 304 is a GPS receiver, the connection to the control unit 302 may be a serial communication link. In another embodiment, the location unit 304 may comprise a GPS daughterboard such as those manufactured by Avocet, Trimble, Ashtech, or Rockwell, for example. If the location unit 304 is a GPS daughterboard, the connection to the control unit 302 is usually through a proprietary connector mounted on the control unit 302. The control of the GPS daughterboard is generally accomplished using a serial connection. In a further embodiment of the invention, the location unit 304 may comprise a GPS chipset or a single GPS chip which is mounted directly on the control unit 302 and which has a bus interface. Furthermore, any of the GPS implementations of the location unit can include differential GPS using RTCM or RTCA corrections or alternatively can include WAAS capabilities.

It is well known to those of ordinary skill in the art that there are a variety of alternative implementations for the location unit that don't involve standard GPS. For example, one can use a distributed GPS system, such as the one developed by SnapTrack, in which part of the GPS functionality is handled by a centralized server. Another alternative location option is the use of a triangulation technique using either angle of arrival or time difference of arrival information. Although the generic term triangulation is used, there is no requirement that three measurement points be used. A further location option is the use of RF fingerprinting, such as that developed by U.S. Wireless, which determines the unit location based on a multipath signature.

Those of ordinary skill in the art will understand that FIGS. 2a–e, 3a–d, and 4a show logical antennas rather than physical antennas. These logical antennas can be combined in virtually any combination into a single physical antenna or groups of physical antennas depending on the specific requirements.

Figure 3B:
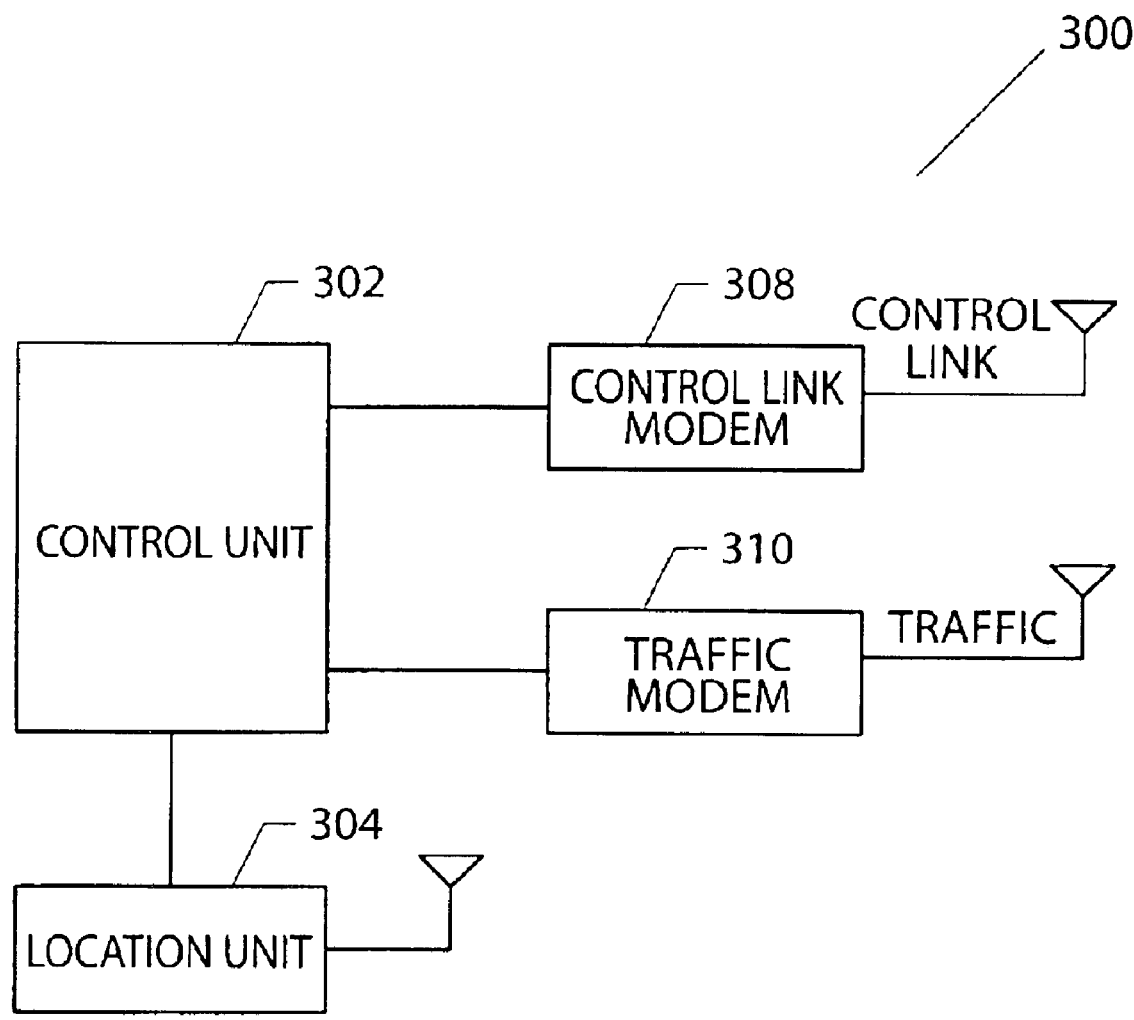

FIG. 3b shows another architecture for the remote unit 300 with separate control link modem 308 and traffic modem 310 in accordance with a further embodiment of the invention. FIG. 3b differs from FIG. 3a in that the single control link and traffic modem 306 has been divided into a separate control link modem 308 and traffic modem 310. The advantage of separating the control link modem 308 from the traffic modem 310 is that it allows the remote unit 300 to communicate control information and traffic information over different communication networks.

It is well known to those of ordinary skill in the art that there are variety of implementations for both the traffic modem and the control link modem that will be referred to collectively as modem units. In one embodiment of the invention, the modem units may comprise a handset that is connected to the control unit using a special serial cable. In an alternative embodiment of the invention, the modem units may comprise a modem module that is connected to the control unit using a special serial cable. In another embodiment of the invention, the modem units may comprise a PCMCIA card that is connected to the control unit using a PCMCIA socket. In a further embodiment of the invention, the modem units may comprise a custom modem that is implemented on either a separate printed circuit board or on the same printed circuit board as the control unit. In another embodiment of the invention, the modem units may comprise a software-defined radio (SDR) in which most of the radio functionality is implemented in software. The software can be running either on a separate printed circuit board or on the same printed circuit board as the control unit. In an alternative embodiment of the invention, the control link modem may comprise a 2-way data device, such as the RIM Blackberry or Motorola CreataLink, which interfaces to the control unit via a serial connection.

The traffic modem 310 is selected so that it can work over a wireless network using a particular wireless standard. For example, the wireless network can be AMPS, iDEN, COMA, TDMA, GSM, ARDIS, MOBITEX, or CDPD. It should be noted that these standards are listed as examples and are not meant to limit the scope of the invention. It is well known to those of ordinary skill in the art that other wireless network standards such as W-CDMA, PHS, i-Burst, NAMPS, ETACS, WLL, UMTS, TETRA, and NMT may also be supported just to name a few more examples.

The traffic modem 310 may implement more than one wireless standard. For example, QUALCOMM manufactures dual mode phones that support both CDMA and AMPS operation. In addition, if the traffic modem 310 is implemented using a software-defined radio then it is possible to implement all of the above-mentioned standards using a single hardware platform.

The control link modem 308 is also selected so that it can work over a wireless network using a particular wireless standard. For example, the wireless network can also be AMPS, iDEN, CDMA, TDMA, GSM, ARDIS, MOBITEX, or CDPD. A primary factor in selecting a wireless standard for the control link modem is the pricing policy for transmitting control link information.

Figure 3C:
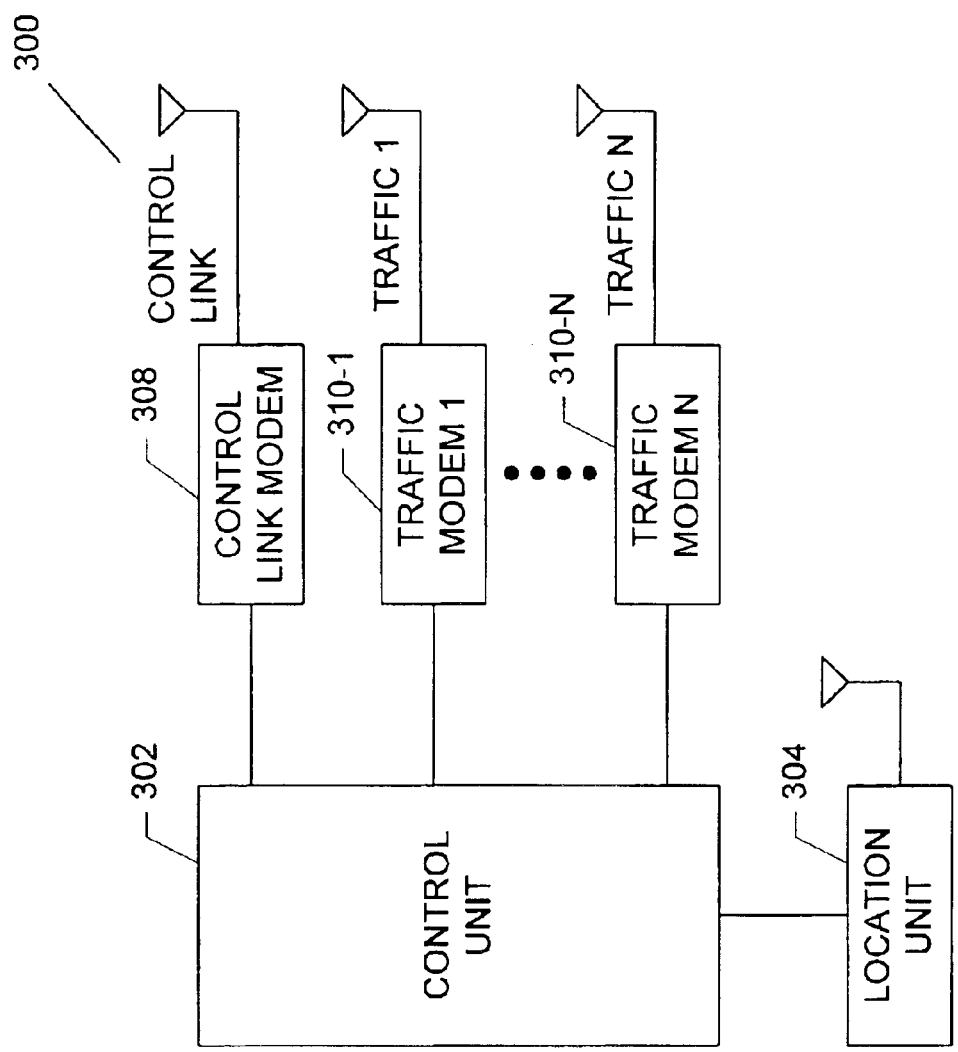

FIG. 3c shows another architecture for the remote unit 300 with a control link modem and multiple traffic modems 310-1–310-N in accordance with a further embodiment of the invention. FIG. 3c differs from FIG. 3b because it includes multiple traffic modems rather than a single traffic modem. The remote unit 300 architecture of FIG. 3c includes a control unit 302 that is connected to a location unit 304, control link modem 308, and traffic modems 1 (310-1) through N (310-N).

Figure 3D:
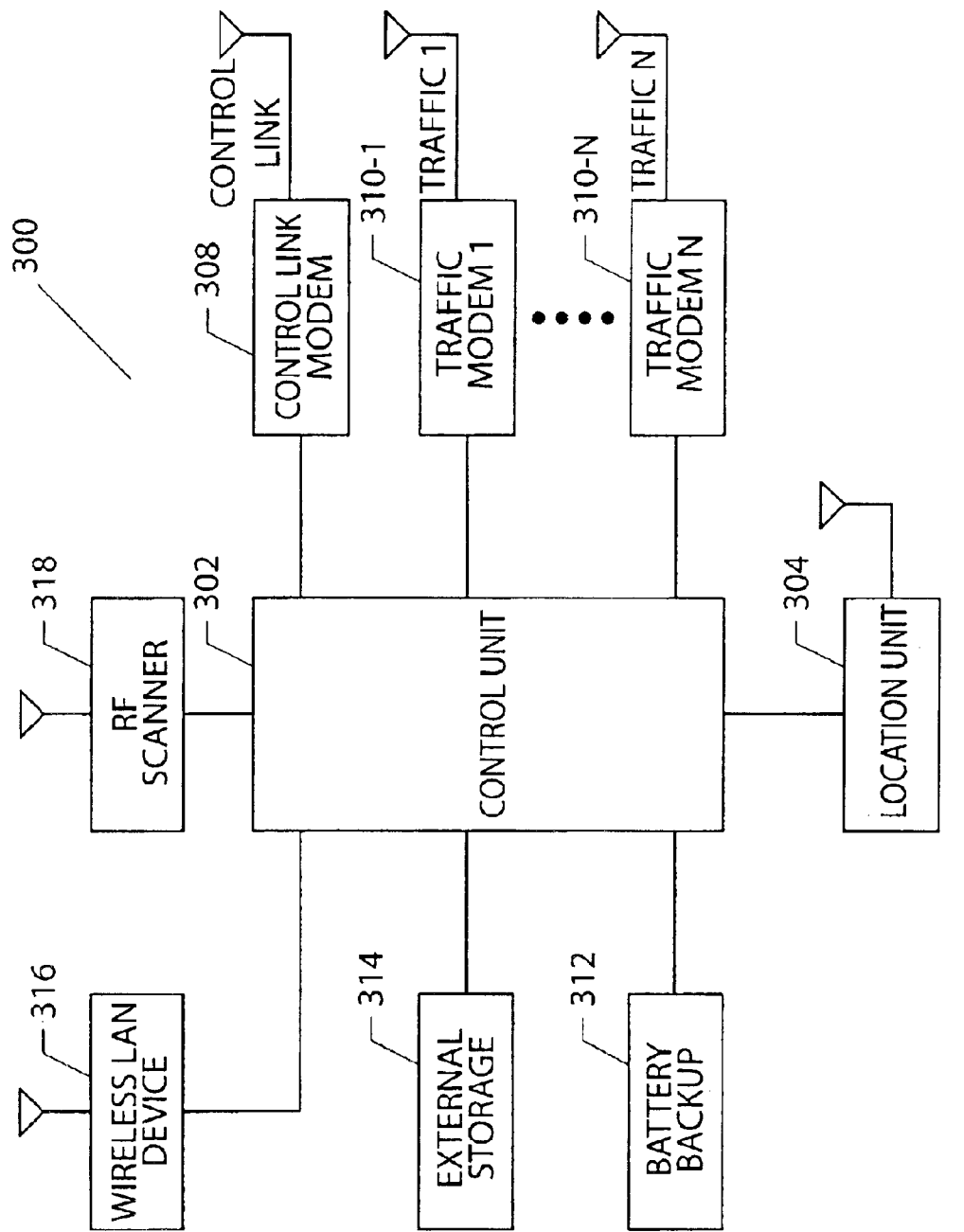

FIG. 3d illustrates a remote unit according to one embodiment of the present invention that includes multiple peripherals. The remote unit 300 architecture of FIG. 3d includes a control unit 302 that is connected to a location unit 304, a control link modem 308, traffic modems 1 (310-1) through N (310-N), battery backup 312, external storage 314, a wireless LAN device 316, and an RF scanner 318. The location unit 304, control link modem 308, and traffic modems 1 (310-1) through N (310-N) are implemented in the same manner as discussed above with reference to FIG. 3c.

The battery backup 312, shown in FIG. 3d, provides power to the remote unit 300 when the main power is not available. If the remote unit 300 is mounted in a vehicle, the battery backup 312 is used when the vehicle ignition is turned off in order to ensure that the remote unit 300 does not drain the vehicle battery while the vehicle is parked. If the remote unit 300 is mounted in a stationary location, the battery backup 312 may be used to provide power if the main power is cut off due to a power failure in the building. In accordance with one embodiment of the invention, the battery backup 312 includes a battery and a battery charger. The battery can be made from a variety of known rechargeable technologies such as sealed lead acid, NiCad, NiMH, and Lithium for example.

The external storage 314 provides a temporary storage capability for data that is not immediately sent back to the back end processor 224. There are a variety of reasons for storing data in the external storage 314. For example, if layer 3 network data is collected for the wireless network it is possible to produce 1 Mbyte/hour/technology of data. It may be prohibitively expensive to send this much data back to the back end processor 224 via the control link modem 308. Accordingly, the data can be stored locally in the external storage 314 and be downloaded at a later time using an alternate path.

As another example, the collected data may be queued for transmission when the vehicle ignition is turned off. It may be preferable not to transmit the stored data until the ignition is turned back on in order to prevent unnecessary draining of the battery backup mechanism 312. Accordingly, the data can be stored locally in the external storage 314 and queued for transmission in at a later time over the control link modem 308 when the vehicle ignition is turned on.

It is well known to those of ordinary skill in the art that the external storage 314 can be implemented in a variety of ways. For example, the external storage is implemented as a PCMCIA Flash card that plugs into a PCMCIA socket on the control unit. As another example, the external storage 314 can be a SANdisk that is connected to the control unit via a proprietary connector. Alternatively, the external storage 314 is implemented using a moving storage device such as a specialized hard drive, for example a PCMCIA hard drive module. However, in mobile environments it is preferable to implement the external storage with no moving parts in order to improve the reliability of the remote unit.

The wireless LAN device 316 allows high-speed data transmission over short distances. In accordance with an embodiment of the invention, the wireless LAN device 316 is implemented, for example, using Bluetooth technology. The wireless LAN device 316 provides an alternative path for downloading data that is stored on the external storage 314. For example, if the remote unit 300 is mounted in a taxi and layer 3 wireless network data is stored from an earlier collection operation, then the wireless LAN device 316 is free to communicate with a wireless LAN controller (not shown) located at the taxi dispatch center in order to transmit the data back to the back end processor 224. As an alternative example, the wireless LAN device 316 can be used to communicate with a local I/O device (not shown) that can be used in a delivery truck to allow communications between a central dispatch and the delivery truck operator.

The RF scanner 318 allows increased functionality for the remote unit 300 by increasing the capabilities for performing RF optimization of the wireless network.

The RF scanner 318 allows the collection of more RF data then is traditionally available through the traffic modems (310-1–310-N). For example, the RF scanner 318 has a much more flexible input bandwidth since it is not forced to listen to a single traffic channel on the wireless network. Additionally, if the RF scanner 318 is optimized for CDMA collection, it can collect a variety of valuable CDMA network parameters such as measuring Io in the channel, despreading the spreading codes, measuring Ec/Io, and measuring chip delay. The RF scanner 318 can be implemented by using a commercial scanner or by developing a custom scanner, for example, using a software-defined radio.

Figure 4A:
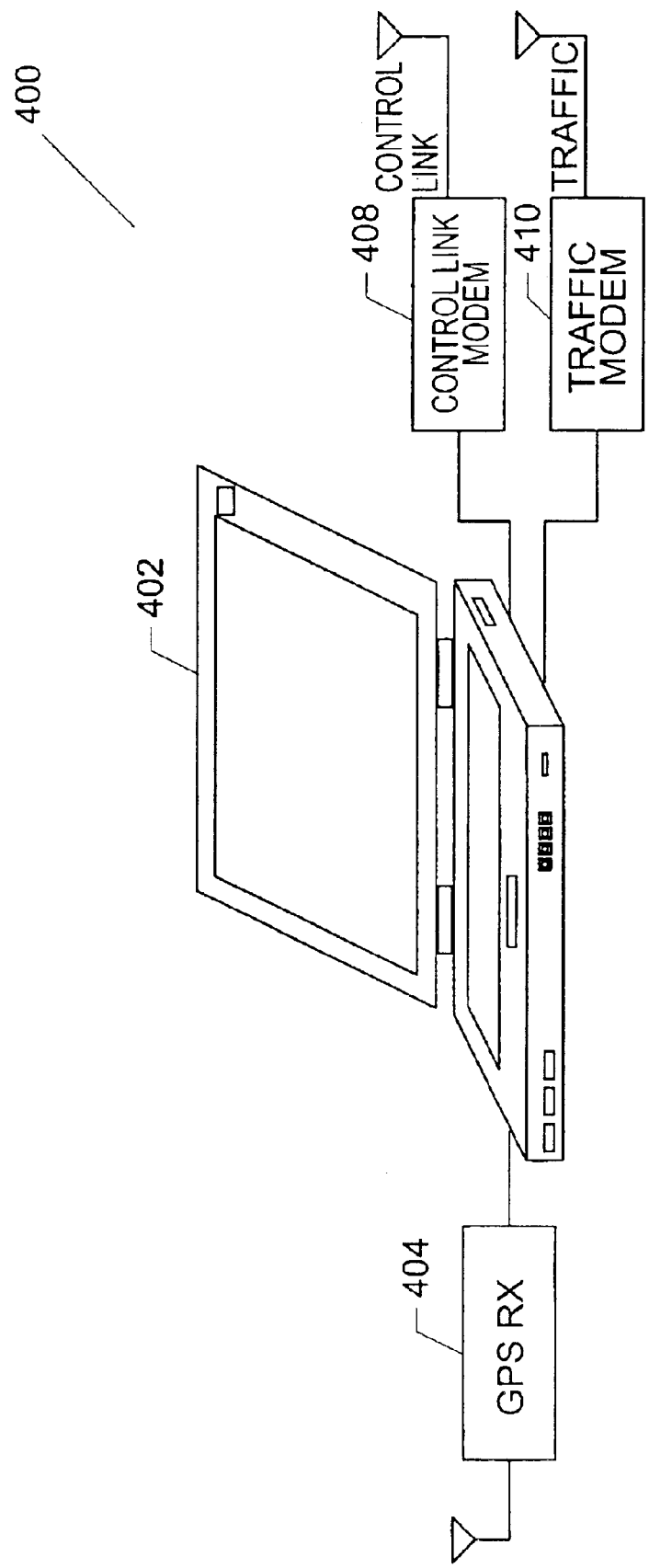
FIGS. 4a through 4d show a variety of alternate implementations for the remote unit in accordance with one embodiment of the invention.

FIG. 4a shows a hardware implementation of the remote unit 400 using either a laptop or handheld unit 402 in accordance with one embodiment of the invention. The laptop or handheld unit 402 is connected to a GPS receiver 404, control link modem 408, and traffic modem 410. The laptop or handheld unit runs any of a variety of operating systems such as Windows 95/NT/CE, Linux, or Palm OS, for example. The peripheral devices 404, 408, 410 are connected to the laptop or handheld unit 402 via serial ports, PCMCIA ports, Ethernet, or USB as appropriate. The laptop or handheld unit 402 should have device drivers for all of the peripheral devices that are either built into the operating system or written in a higher-level language. Furthermore, the laptop or handheld unit 402 runs a main program that allows extraction of the location information from the GPS receiver 404 and sends and receives communication over the control and traffic channels.

Figure 4B:
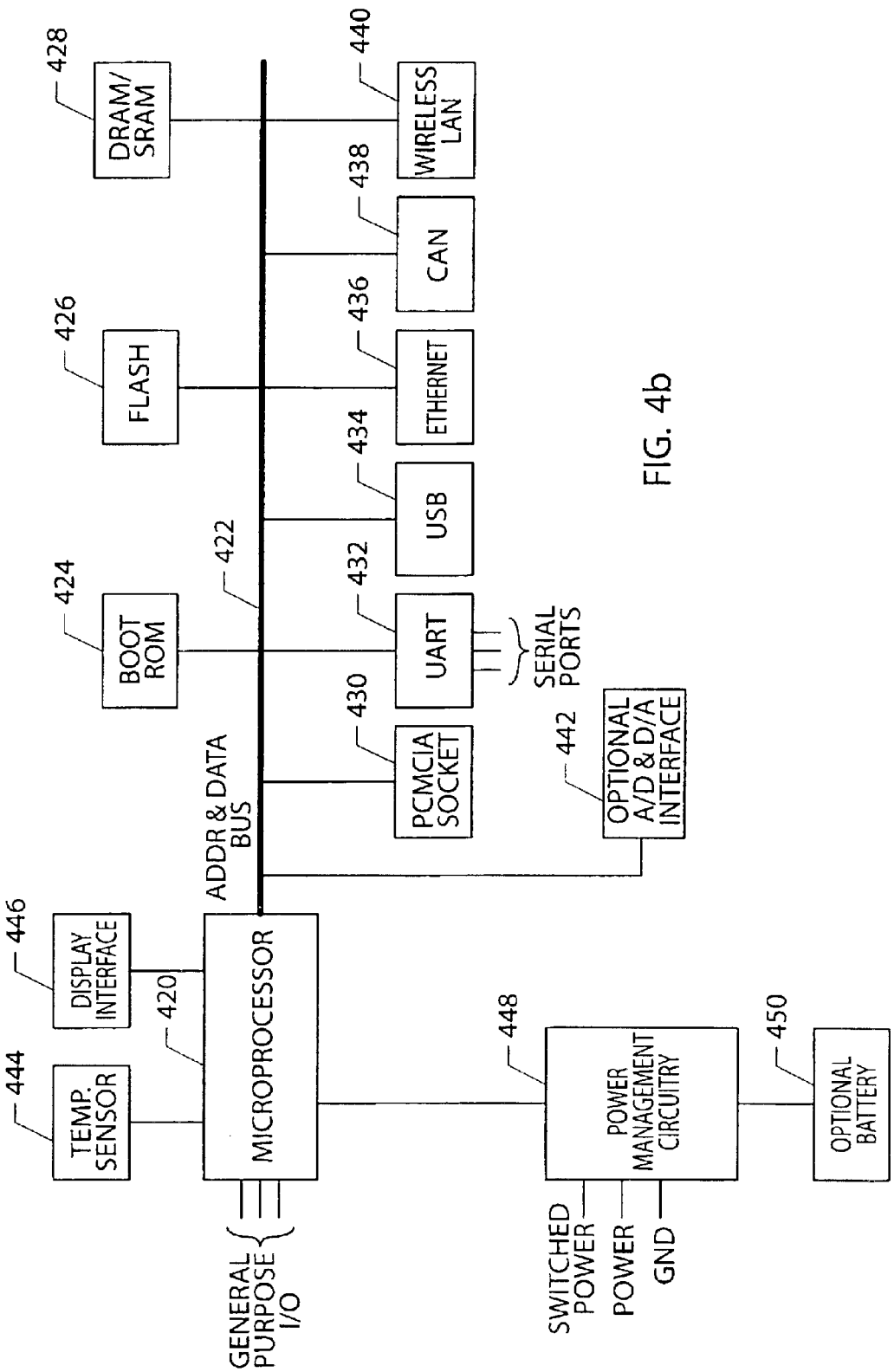

FIG. 4b shows a hardware implementation of the remote units using a single board computer (SBC) in accordance with one embodiment of the invention. The single board computer can be purchased off-the-shelf from a variety of vendors such has SBS, ADS, or Datalogic for example. Alternatively, the single board computer can be custom designed for the specific remote unit application. FIG. 4b shows a typical architecture for the single board computer including a microprocessor 420 which is connected via an address and data bus to a boot ROM 424, Flash memory 426, DRAM/SRAM 428, a PCMCIA socket 430, a UART 432, a USB interface 434, an Ethernet interface 436, a CAN interface 438, a wireless LAN device 440, and an optional A/D & D/A interface 442. The microprocessor 420 may also have direct connections to a temperature sensor 444, display interface 446, and general-purpose I/O. Additionally, the single board computer may include power management circuitry 448 that is connected to switched power, power, and ground, and additionally connected to an optional backup battery 450.

It is well known to those of ordinary skill in the art that the single board computer can be implemented using a variety of different technologies. For example, the microprocessor can be a StrongARM, ARM, Pentium, PowerPC, Motorola 68000, and the like. Furthermore, a variety of operating systems are available such as Windows CE, Windows 95/98, Windows NT, Linux, Palm OS, VXWorks, OS-9, PSOS, and the like. The serial ports from the UART 432, or directly from the microprocessor 420, are used to interface to peripheral devices such has the traffic modem 410 or the GPS receiver 404 and should have configurable bit rates, word size, start bits, stop bits, parity bit and the ability to operate at either TTL or RS-232 voltage levels.

Figure 4C:
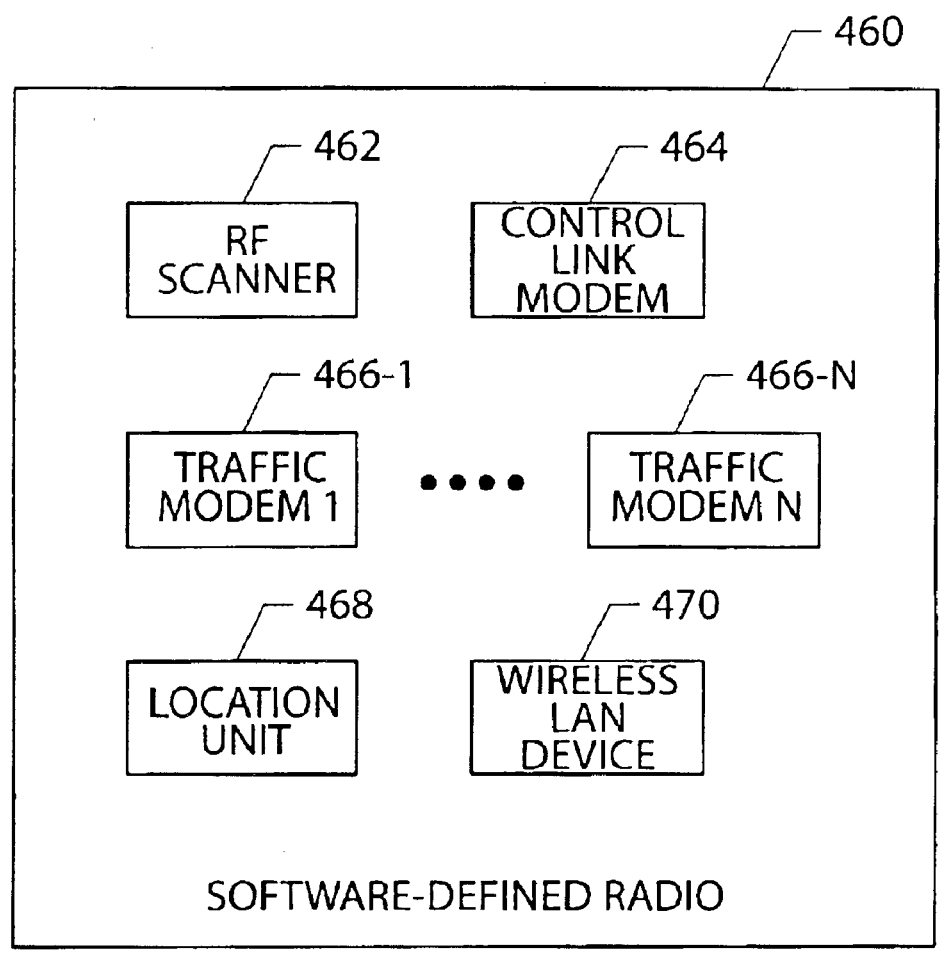

FIG. 4c shows the organization of a software-defined radio in accordance with an alternate embodiment of the invention. All of the elements of the software-defined radio 460 can be combined in any combination depending on the requirements. The elements include an RF scanner 462, a control link modem 464, traffic modems 1 (466-1) through N (466-N), a location unit 468, and a wireless LAN device 470. The advantage of using a software-defined radio architecture is that it allows implementation of multiple standards simultaneously on a single hardware device. This can greatly reduce the cost of the remote unit. The underlying architectural concepts for the software-defined radio 460 are well known to those of ordinary skill in the art and are discussed in articles in numerous journals such as the IEEE Communications Magazine.

Figure 4D:
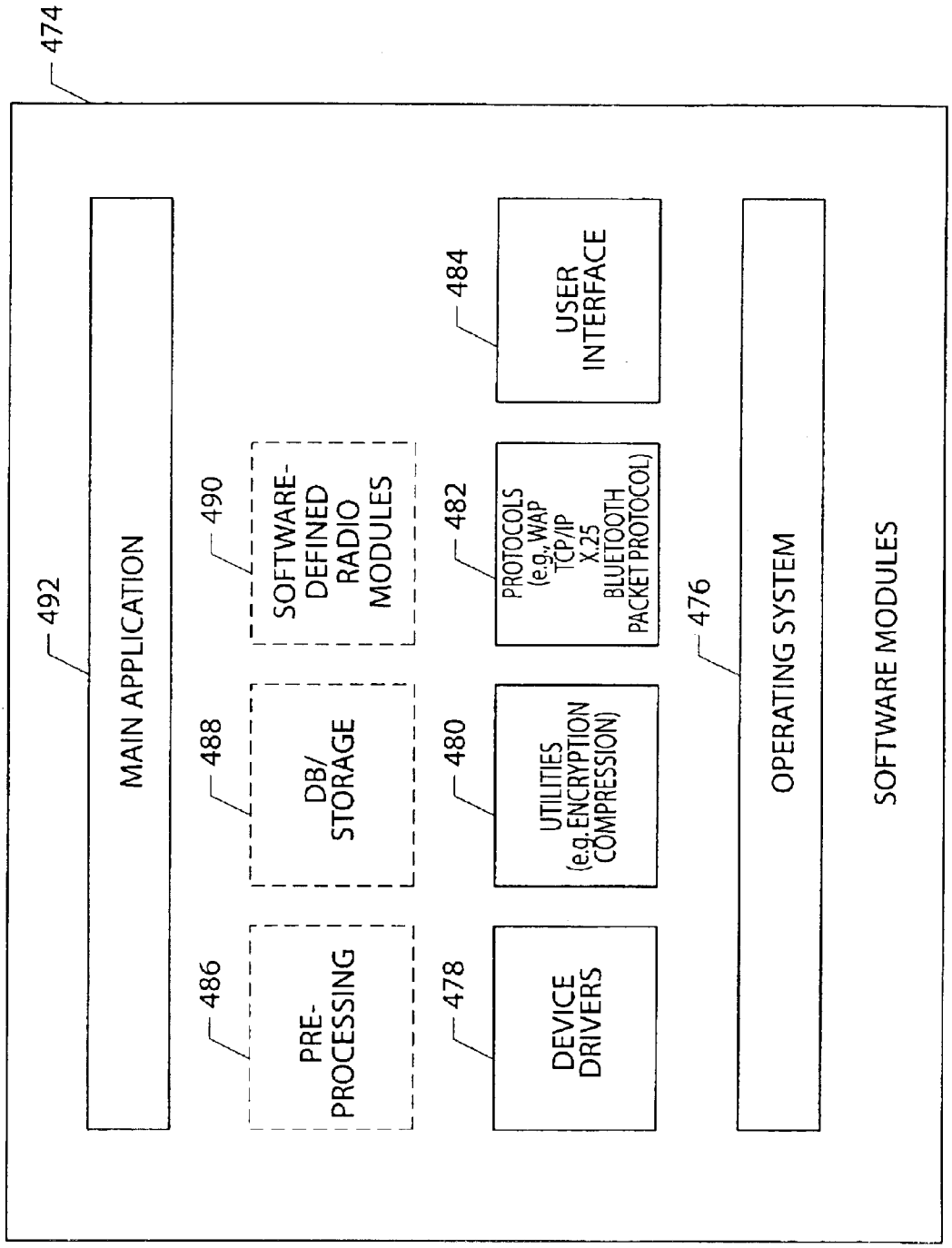

FIG. 4d illustrates organization of the software in the remote unit in accordance with an embodiment of the invention. At the lowest level is the operating system 476 that provides basic functionality for the hardware platform. The remote unit can run a variety of operating systems such as Windows 95/NT/CE, Linux, Palm OS, VXWorks, QNX, or pSOS for example. Furthermore, depending on the requirements, it is possible to use no operating system and write platform-specific code to implement the lower level routines.

At the next level, the remote unit software includes device drivers 478, utilities 480, protocols, 482 and user interface modules 484. The device drivers 478 allow communication with the peripheral devices such as the GPS receiver 404 and the wireless modems, for example. The utilities 480 support lower-level functions such as encryption and compression, for example. The protocols 482 support any protocols that are needed in the remote unit such as a WAP browser, TCP/IP, X.25, and any proprietary packet protocols, for example. The user interface module 484 includes all of the functionality required for local control of the remote unit such as a simple menuing system. It is well known to those of ordinary skill in the art that some or all of these modules may also be built into the operating system.

At the next level, the remote unit software optionally includes a variety of additional modules such as a pre-processing module 486, DB/Storage module 488, and a software-defined radio module 490. The pre-processing module 486 may be used to pre-process the collected data. This is particularly helpful in an operational scenario in which large quantities of data are collected and need to be reduced in order to conserve control link bandwidth. The DB/Storage module 488 may be used to store and organize the requested missions and/or the collected data. The software-defined radio module 490 is implemented as described above with reference to FIG. 4c.

The main application 492 is at the next level and performs the higher-level routines. For example, the main application 492 is used to receive missions over the control link, execute the missions, and transmit the mission data over the control link.

In the implementations described above, the control unit 302 is shown as being a general purpose computer in the form of a laptop or handheld unit 402. Although this has certain advantages in terms of flexibility of programming, the invention may also be implemented using special purpose computers in lieu of general purpose computers.

Back End Processor

Figure 5A:
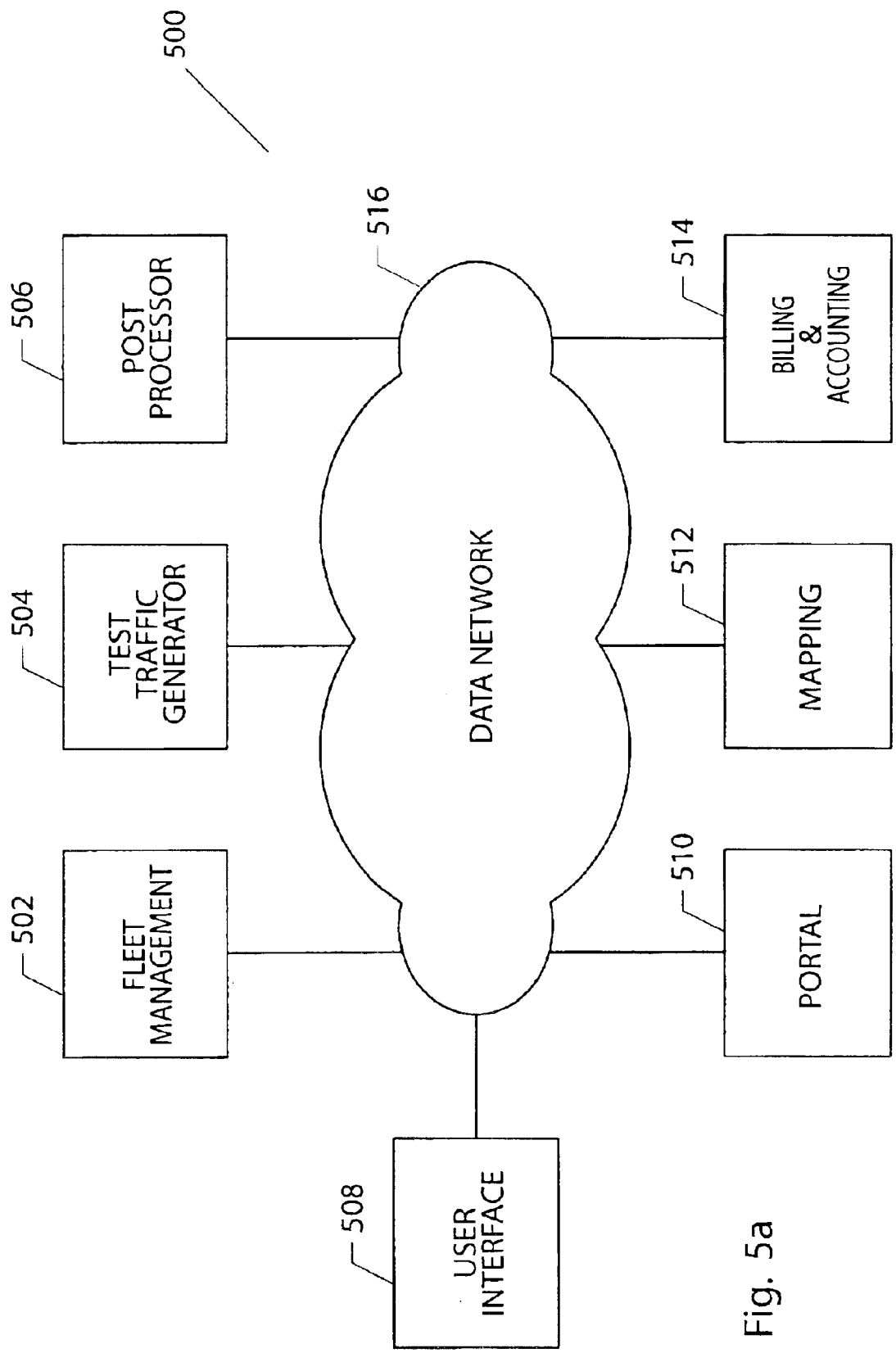
FIG. 5a shows the architecture of the back end processor in accordance with one embodiment of the invention.

FIG. 5a shows the architecture of the back end processor 500 in accordance with one embodiment of the invention. The back end processor 500 includes the following processing elements: fleet management 502, test traffic generator 504, post processor 506, user interface 508, portal 510, mapping 512, and billing and accounting 514. These processing elements are interconnected by a data network 516. It is well known to those of ordinary skill in the art that the data network 516 can be either a LAN, WAN, inter processing communications within a computer or network, or any combination of the above.

Figure 5B:
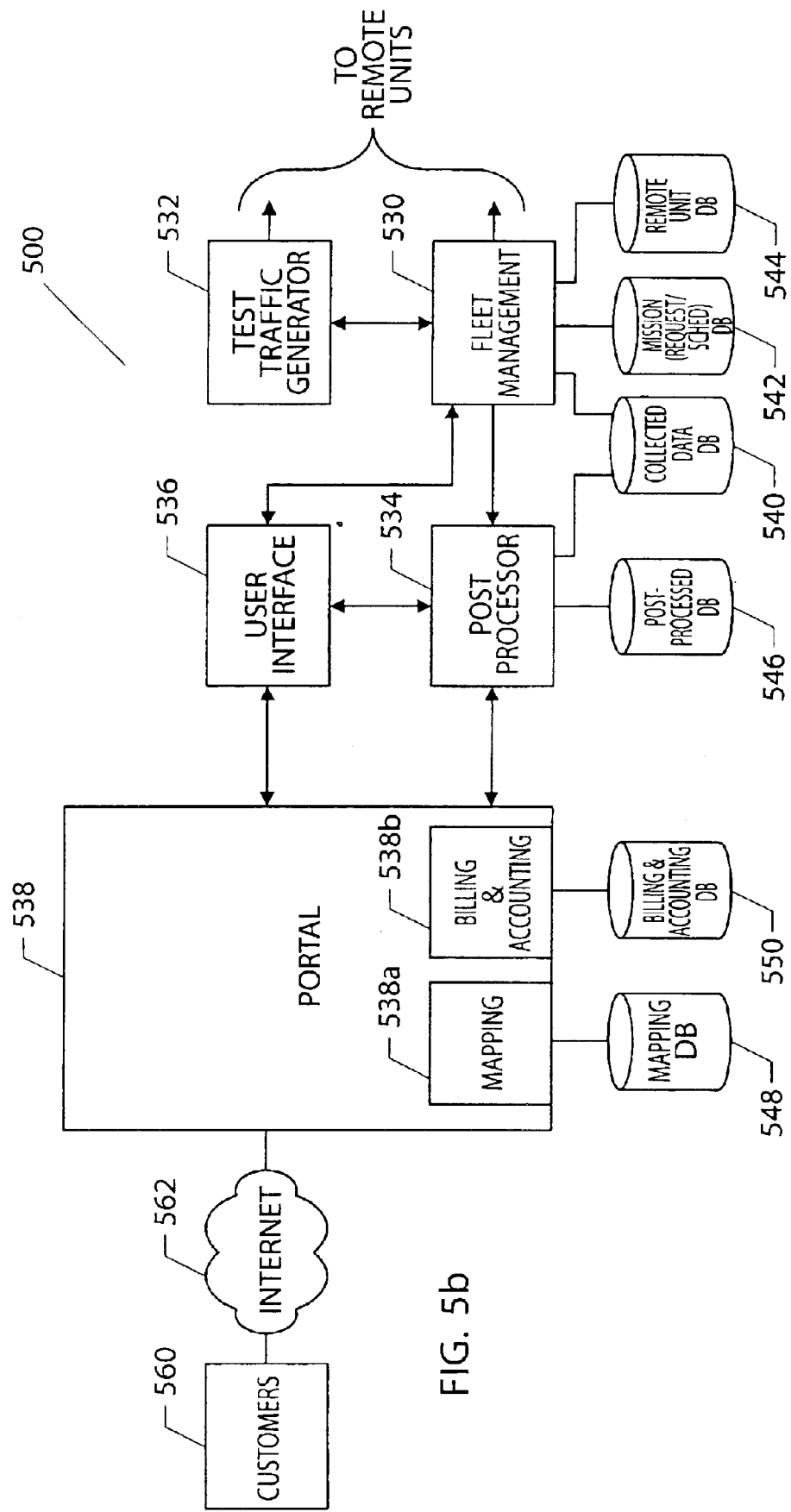
FIG. 5b shows the architecture of the back end processor in accordance with an alternate embodiment of the invention.

FIG. 5b shows the architecture of the back end processor 500 in accordance with a further embodiment of the invention. The back end processor includes the following processing elements: fleet management 530, test traffic generator 532, post processor 534, user interface 536, and portal 538 including a mapping element 538a and a billing and accounting element 538b. In addition, the fleet management element 530 is connected to a collected data database 540, mission database 542, and remote unit database 544; the post-processing element 534 is connected to a post-processed database 546 and the collected data database 540, and the portal 538 is connected to a mapping database 548 and a billing and accounting database 550.

The fleet management element 530 is the main interface in the back end processor for communicating with the remote units. The fleet management element keeps track of the remote units by accessing data in the remote unit database 544, performs mission planning and coordination based upon information provided from the user interface 536, sends and receives information to the test traffic generator 532 in order to generate terrestrial originated calls, and sends and receives commands and responses to the remote units via the control link.

The fleet management element 530 receives mission requests from the user interface 536 and stores the information in the mission database 542. It then performs a scheduling function based on the requested missions stored in the mission database 542 as compared with the remote units available as determined by availability information stored in the remote unit database 544. The scheduled missions are stored in the mission database 542 as requested missions and are sent at the appropriate time to the remote units over the control link. The requested missions can be stored and sent as a batch of missions or can be sent as individual missions depending on the requirements.

The information received by the fleet management element 530 is stored in the collected data database 540 and forwarded to the post processor element 534 that stores raw mission data and also performs post processing and stores the post processing results.

The post processing involves processing of the received data for either RF/network parameters related to the wireless system or statistical information related to the wireless data access.

The analysis of the RF/network parameters can be accomplished in a variety of ways such as those discussed in Provisional Patent Application No. 60/149,888 entitled "Wireless Telephone Network Optimization" that was filed on Aug. 19, 1999, and which is incorporated by reference herein in its entirety for all purposes. This provisional disclosure provides a simulation environment to develop optimum coverage-related parameters for sectors of a wireless network. This simulation environment allows a network engineer to vary parameters of a virtual model of the wireless network and observe how the changes affect coverage. The provisional disclosure further provides an optimization algorithm to optimize hand off timing parameters for sectors in a wireless network. The optimization algorithm analyzes measured data regarding network coverage and regional terrain to arrive at a report containing recommended values for window size parameters (code division systems) or time advance parameters (time division systems).

The post processing for statistical analysis involves the wireless data access that is accomplished using the traffic modem in the remote unit. The statistical analysis allows the combination of various collected information in order to produce reports for specific customers. For example, the latency of WAP accesses to a specific URL is measured over several different wireless networks and displayed on a bar graph. Further examples of statistical analysis and report generation are discussed in the operation section with respect to FIGS. 8a–8f.

The user interface element 536 is connected to the fleet management element 530 in order to schedule missions based on requirements entered by the customers. Additionally, the user interface element 536 is connected to the post processing element 534 to allow users to generate special queries, access previously stored queries, or access reports that are generated from the post processed data. The user interface element 536 is also connected to the portal 538 to allow access for the customers 560 from a connected data network such as the Internet 562.

The portal element 538 acts as an operating system providing a variety of low-level functions for multiple applications. The portal 538 includes a mapping element 538a and a billing and accounting element 538b. The portal 538 is connected to databases 548, 550 for the mapping information and the billing accounting information. In addition, the portal 538 is connected to the data network 562, such as the Internet, to allow customer entry into the system. The portal is also connected to the post processor 535 to allow access of the post-processed data for visualization with the mapping software, for example.

Figure 5C:
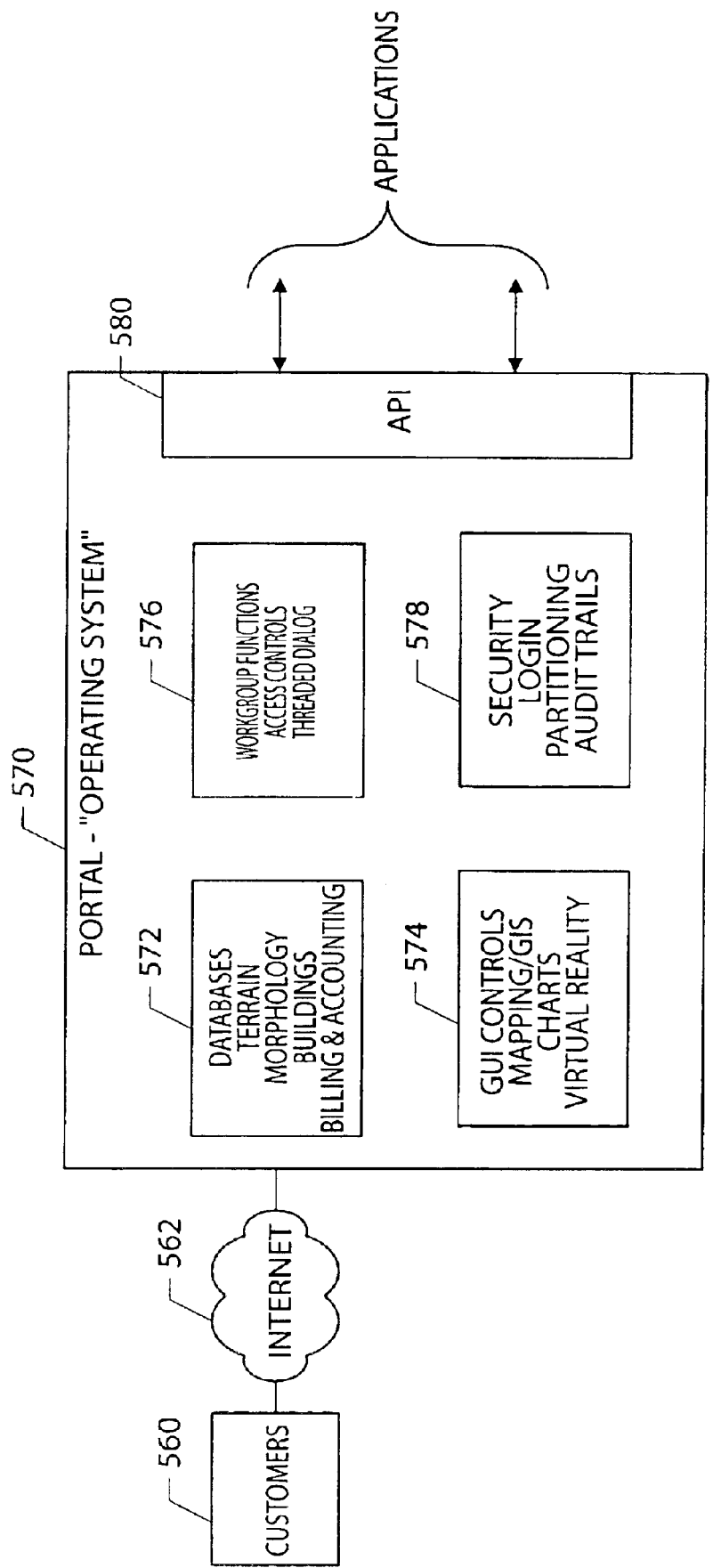
FIG. 5c shows the architecture for the portal in accordance with one embodiment of the invention.

FIG. 5c shows the architecture for the portal 570 in accordance with one embodiment of the invention. The portal 570 acts as an operating system providing common low-level functions for a variety of applications and acting as an interface for customer access through the Internet. The portal 570 functions are organized into four major groups: databases 572, GUI controls 574, workgroup functions 576, and security 578. The database 572 functions include terrain, morphology, buildings, and billing and accounting. The GUI controls 574 include mapping/GIS, charts, and virtual reality. The workgroup functions 576 include access controls and threaded dialogue. The security functions 578 include login, partitioning, and audit trails. The portal also includes an API 680 that allows access to various applications.

Control Link Communication Protocol

The control link allows communications between the multiple remote units and the back end processor. There are a variety of possible protocols for the control link. The communication protocol can be a standard protocol such as TCP/IP, WAP, or X.25, for example, or a proprietary protocol that is optimized for the required communications, or some combination of a standard and proprietary protocol.

In accordance with one embodiment of the invention, a proprietary packet protocol is used. One issue regarding the packet protocol is the issue of acknowledgments for packets.

Acknowledgments can be handled in a variety of ways. They can be sent as an individual packet for each substantive packet sent. This is the heartiest mechanism but it is bandwidth inefficient. Alternatively, acknowledgments can be sent as a field of a subsequent packet using a packet numbering scheme to indicate which previous packet is being acknowledged. This method requires more overhead at each end of the communication link in order to keep track of previously sent packets, but is more efficient in terms of bandwidth used. As another alternative, the acknowledgment system can be handled by the communication system itself so that the packet protocol does not have to address the issue. For example, many two-way data systems have a built-in acknowledgment system so that packet delivery is virtually guaranteed. In this case, it is not required to include acknowledgments in the packet protocol since they are handled at another level.

There are two basic types of packets: signaling packets and data packets

The signaling packets are originated either at the remote unit or at the back end processor. Some examples of remote unit originated packets are ignition on, ignition off, and status update. The Ignition on packet indicates that the vehicle ignition has been turned on and the ignition off packet indicates that the vehicle ignition has been turned off. These packets are used by the back end processor in order to properly schedule data collection in a mobile remote unit. The status update packet indicates the current status of the remote unit.

Some examples of back end originated packets are reset and status request. The reset packet is used to remotely reset the remote unit. The status request packet is used to remotely request status information for a remote unit.

The data packets are also either originated at the remote unit or at the back end processor. The back end originated data packets generally consist of mission requests and the remote unit originated data packets generally consist of mission data.

Figure 6A:
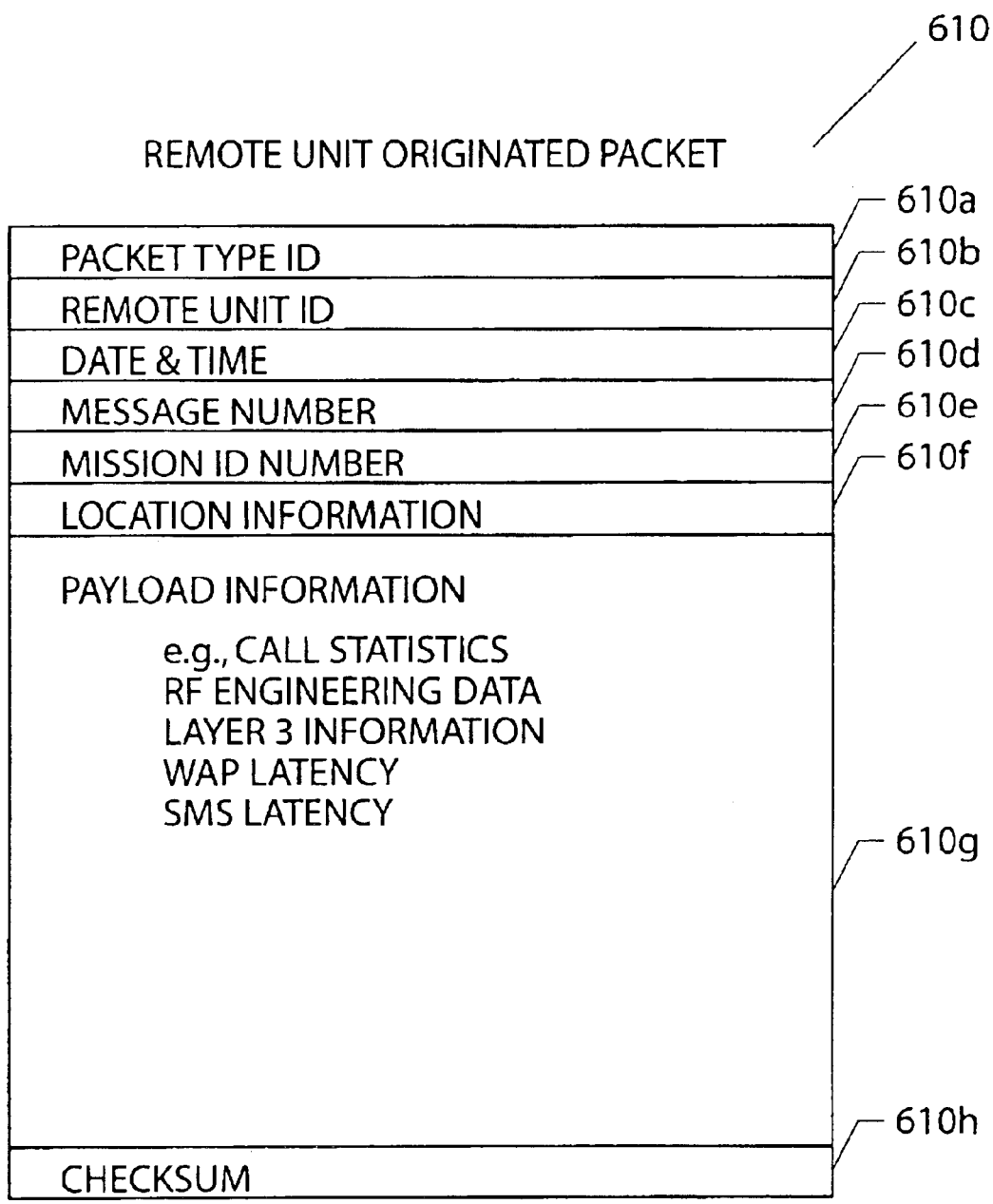
FIG. 6a shows examples of some of the fields in the remote unit originated packets (both data and signaling) in accordance with one embodiment of the invention.

FIG. 6a shows examples of some of the fields in the remote unit originated packets (both data and signaling) 610 in accordance with one embodiment of the invention. Some examples of the packet fields include a packet type ID 610a, remote unit ID 610b, date and time 610c, message number 610d, mission ID number 610e, location information 610f, payload information 610g, and checksum information 610h. The packet type ID field 610a indicates the type of packet so that the back end processor will know how to parse the packet for the proper fields. The remote unit ID field 610b is used to identify the remote unit sending the packet. The date and time field 610c indicates the date and time that the measurement is taken. The message number field 610d is used to keep track of the message for acknowledgment purposes. The mission ID number field 610e is used by data packets to indicate the corresponding back end mission that caused generation of the packet's payload information. The location information field 610f indicates the remote unit location at the time of data collection. The checksum information field 610h is used in order to ensure the integrity of the packet information. The term checksum is used generically to refer to any type of error correction and/or error detection method to ensure packet integrity.

The remote unit originated data packet's payload information field 610g can take a variety of forms. It may include call statistics such as connect time, call duration, whether the call failed to connect or was dropped, and the like. Additionally, it may include basic RF engineering measurements such as RSSI, BER, FER, SQE, and the like. Furthermore, the payload information may include Layer 3 information that discloses call routing data and information regarding the configuration of the wireless network. The Layer 3 information may be collected in totality or filtered by pre-processing in the remote unit depending on the amount of information desired. In addition, the payload may include application information such as the access latency for a WAP page or the delay in receipt of an SMS message.

Figure 6B:
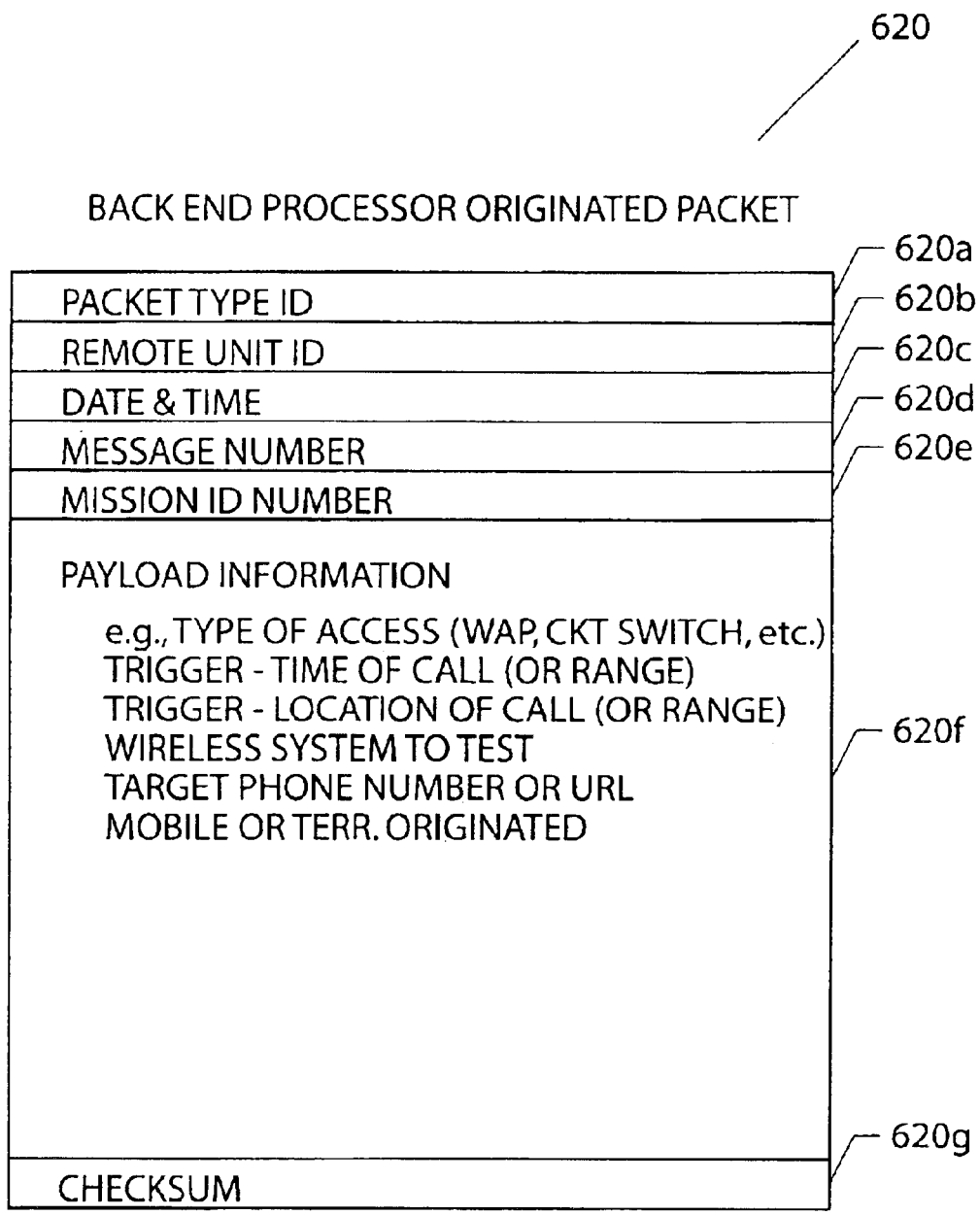
FIG. 6b shows examples of some of the fields in the back end processor originated packets (both data and signaling) in accordance with one embodiment of the invention.

FIG. 6b shows examples of some of the fields in the back end processor originated packets (both data and signaling) 620 in accordance with one embodiment of the invention. Some examples of the packet fields include a packet type ID 620a, remote unit ID 620b, date and time 620c, message number 620d, mission ID number 620e, payload information 620f, and checksum information 620g. The packet type ID field 620a indicates the type of packet so that the remote unit will know how to parse the packet for the proper fields. The remote unit ID field 620b is used to identify the remote unit receiving the packet. The date and time field 620c indicates the date and time that the packet is sent. The message number field 620d is used to keep track of the message for acknowledgment purposes. The mission ID number field 620e is used by data packets to indicate the back end mission that will cause generation of the packet's payload information. The checksum information field 620g is used in order to ensure the integrity of the packet information. The term checksum is used generically to refer to any type of error correction and/or error detection method to ensure packet integrity.

The back end processor originated data packet's payload information field 620f can take a variety of forms. It may include mission info regarding the type of data to collect including the type of access (WAP, circuit switched data, etc), a trigger related to the time (or range of times) to make the test call, a trigger related to the location (or range of locations) to make the test call, a wireless system to test (if the remote unit supports multiple wireless traffic standards), a target phone number or URL, and whether the call is mobile or terrestrial originated.

It should be noted that the packet field types described above are for illustrative purposes and in no way limit the actual fields that may be used.

The information in the packet can be sent as either ASCII or binary data. ASCII is useful since some two-way data systems are used for paging and will only pass ASCII text information. Binary storage is useful because it is more bandwidth efficient than ASCII. Furthermore, the packet information can be compressed by a variety of standard methods such as null compression, run-length compression, keyword encoding, adaptive Huffman coding, Lempel-Ziv coding, and the like. Additionally, the packet information can be encrypted by a variety of standard methods such as DES, triple DES, RSA, PGP, and the like.

In accordance with one embodiment of the invention, the packets are combined in larger files for transmission over the control link. This is advantageous in an environment in which the control network charges a fixed charge per packet. Accordingly, larger files may be more cost effective. Furthermore, it may be advantageous to store the collected information at the remote unit for transmission at a later time. This can occur if Layer 3 information is collected since the data may be collected faster than it can be sent over the control link. Additionally, the collected information may be stored at the remote unit if the vehicle ignition is turned off during a mission in a mobile environment. This occurs because the system tries to reduce transmissions when the ignition is off in order to extend battery life.

Method for Measuring

Figure 7A:
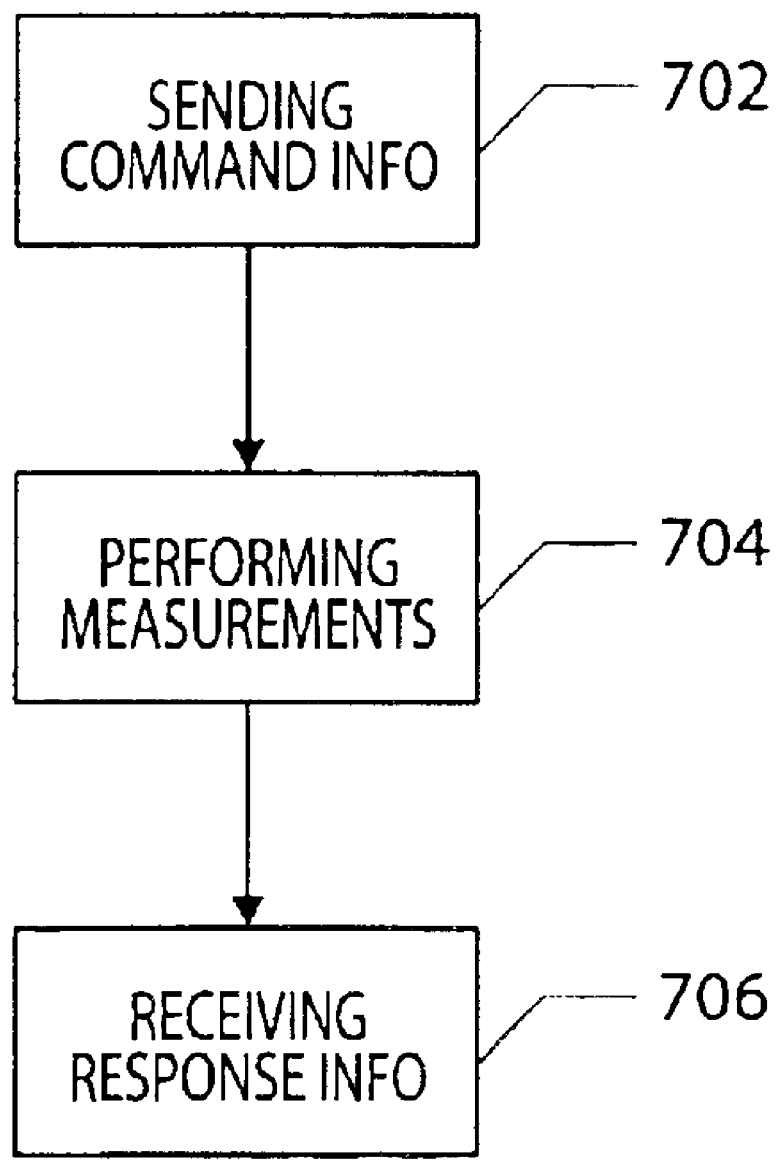
FIG. 7a shows a method for measuring data quality of service in a wireless network in accordance with one embodiment of the invention.

FIG. 7a shows a method for measuring data quality of service in a wireless network in accordance with one embodiment of the invention. The method includes the steps of sending command information 702, performing measurements 704, and receiving response information 706.

For example, the step of sending command information 702 may include using a back end processor to send either data or signaling packets to the remote units of a measuring system such as the one described previously. Furthermore, the step of performing measurements 704 may include performing any of a variety of measurements such as latency of wireless Internet access, e-commerce transactions, wireless messaging, or push technologies. The step of receiving response information 706 may include responses to status inquiries or data related to the measurements collected during the step of performing measurements 704.

Figure 7B:
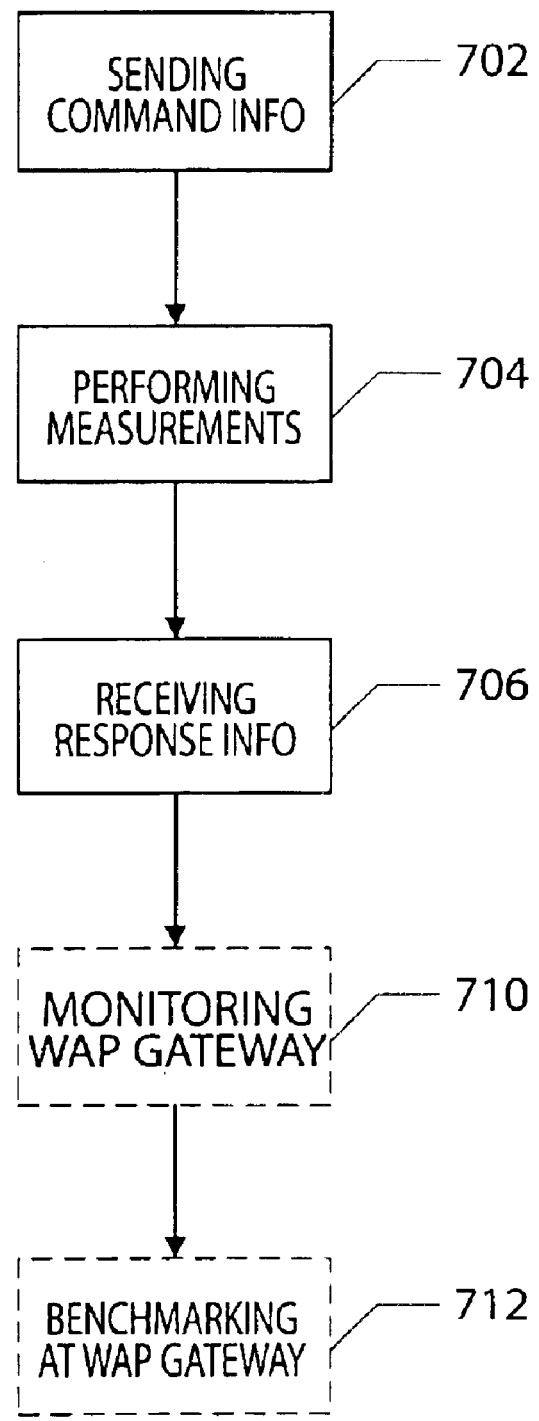
FIG. 7b shows a method for measuring data quality of service in a wireless network, including at least one step related to the wireless network infrastructure, in accordance with an alternate embodiment of the invention.

FIG. 7b shows a method for measuring data quality of service in a wireless network, including at least one step related to the wireless network infrastructure, in accordance with a further embodiment of the invention. The method includes the sending 702, performing 704, and receiving 706 steps described with respect to FIG. 7a. Additionally, the method includes steps of monitoring a WAP Gateway 710 and Benchmarking at a WAP Gateway 712.

The step of monitoring the WAP Gateway 710 may include monitoring traffic through the WAP Gateway and providing metrics such as throughput, latency and lost packet information. Furthermore, the monitoring step 710 may allow the collection of protocol information directly from the WAP Gateway that may not be available to the multiple remote units. The step of benchmarking at the WAP Gateway 712 may allow latency measurements without including the uncertainties of the latency through the Internet or data network itself. This allows the provision of data indicating a breakdown between the latency of the wireless network and the data network.

It is important to note that in regard to steps 710 and 712 that the closeness to the WAP gateway is described from a logical, not a physical, standpoint. It will be appreciated by those of ordinary skill in the art that these process steps can be accomplished with well known techniques in which the monitoring or benchmarking element is located far away from the WAP gateway. Furthermore as previously discussed, the term WAP is being used generically to describe any type of wireless Internet protocol, including HDML, WAP competitors, and any future wireless Internet protocols that may be developed.

Figure 7C:
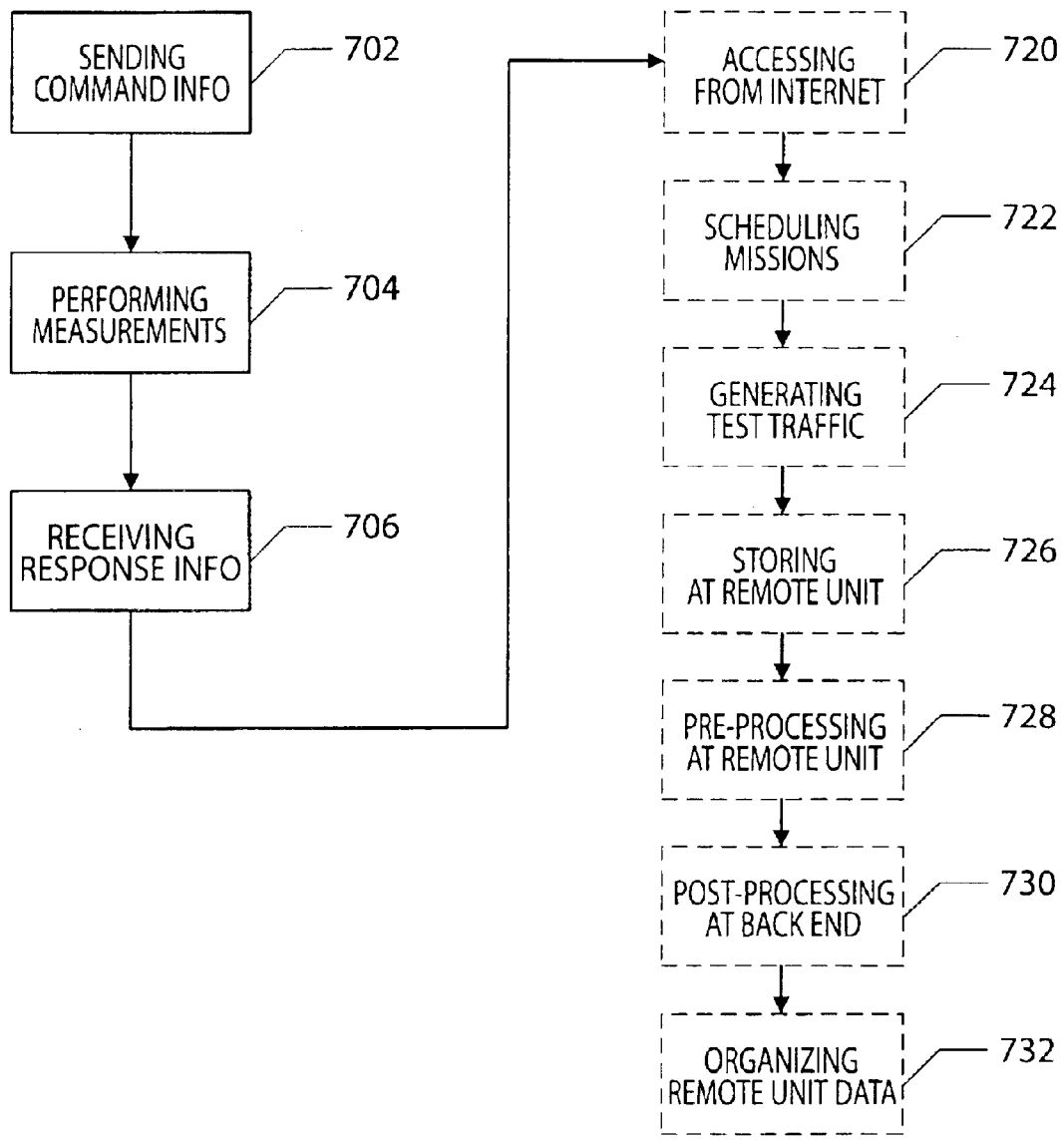
FIG. 7c shows a method for measuring data quality of service in a wireless network, including at least one additional order independent step, in accordance with another embodiment of the invention.

FIG. 7c shows a method for measuring data quality of service in a wireless network, including at least one additional order independent step, in accordance with another embodiment of the invention. The method includes the sending 702, performing 704, and receiving 706 steps described with respect to FIG. 7a. Additionally, the method includes steps of accessing from the Internet 720, scheduling missions 722, generating test traffic 724, storing at a remote unit 726, pre-processing at a remote unit 728, post-processing at the back end 730, and organizing remote unit information 732.

The step of accessing from the Internet 720 may include the ability to access the measuring system from the Internet through a portal to set up missions and retrieve reports generated from the post-processed data, for example. The step of scheduling missions 722 may include establishing parameters related to the specific data to be collected by the system. For example, these parameters may include some of the following: type of access—WAP, SMS, Instant Messaging, Push data, and the like.; type of Device—WAP, PDA, Pager, wireless modem, and the like.; trigger—time of call, location of remote unit, or some combination; wireless system—Sprint, Nextel, AT&T, and the like.; call Info—Target phone#, URL, type of transaction, etc; and mobile or terrestrial originated call. The step of generating test traffic 724 may include generation of SMS messages or other data packets to be sent to the remote units, for example.

The step of storing at the remote unit 726 may include the storing of missions and of collected data at the remote unit. The step of pre-processing at the remote unit 728 may include processing received data prior to storing the data or transmitting it to the back end processor. The step of post-processing at the back end 730 may involve processing of the received data for either RF/network parameters related to the wireless system or statistical information related to the wireless data access. The step of organizing remote unit information may include storage of remote unit identification information in a remote unit database, storage of collected data in a collected data database, or storage of post-processed data in a post-processed data database, for example.

It should be noted that the flow arrows in FIGS. 7a–7c are shown merely for illustrative purposes and do not reflect a required order for the method steps.

Operational and Business Model

The previous sections of this description have discussed a method and system for measuring data quality of service in a wireless network using multiple remote units and a back end processor. The method and system may also include an element that is located within the wireless network infrastructure, for example, at the WAP gateway to monitor the wireless data protocol and to perform benchmarking measurements.

In light of those previous sections, the following section discloses the operational and business model for the system in accordance with a further embodiment of the invention.

Rather than selling measurement equipment as a final product, the system, as defined by the invention, preferably sells the collected data and statistics is generated from the collected data as the final product. The trade name for this service is preferably "Bitwise." The data and statistics generated by the system do not need to be real-time, but as previously disclosed the system will support near real-time data if desired. Typically, the data will be collected and analyzed over a period of time such as a day, week, month, or even a year depending on the user's requirements.

The types of data collected include latency, call statistics (such as call completion, call dropped, etc), BER/FER, and various wireless network parameters such as RSSI and Layer 3 information. For example, the latency time is a measure of the access time for a WML page from a WAP server or the time to complete a Web transaction. Furthermore, the system can divide the latency measurement into the wired network and wireless network contribution through the use of a component located at the WAP gateway.

Furthermore, the remote units can be used to perform additional functions that have value in vertical markets. For example, if the remote units are fielded in a mobile environment in a fleet of vehicles, the remote units can provide automatic lo vehicle location (AVL) in addition to data quality of service measurements. Additionally, the position data from the mobile remote units could be processed to provide near real-time traffic information which could be disseminated, for example, over the Internet.

There are a variety of possible pricing strategies for the data and statistics produced by the system. The user may be charged per minute of system use or per transaction. Alternatively, the user may be charged per city, per wireless carrier, and per month for the requisite data and statistics. Furthermore, the post-processing element produces aggregate industry-wide statistics, for example comparing different wireless carriers or content providers, which is preferably packaged and sold as a separate product.

The customers for the system have a variety of common attributes. They are dot.com and e-commerce companies that are targeting wireless device users by porting their content and commerce to wireless web sites. Furthermore, they generally have a need for timely dissemination of content and transactions and have a keen interest in a positive customer experience.

The customers can be divided into a variety of different groups. They can be wireless operators who wish to measure the performance of their networks in order to increase traffic and optimize performance. Furthermore, the customers can be wireless portals and/or ISPs such as AOL, Yahoo, Alta Vista, MSN, Lycos, and Excite, just to name a few examples. Additionally, the customers can be content providers in a variety of fields such as the service arena providing financial, weather, or traffic content; the internet auction arena involving time-sensitive bidding information; the instant messaging arena such as the AOL Anytime, Anywhere program; and the push data technology arena in which information such as airline information and traffic updates are pushed to the mobile device.

The reasons that customers would use the system, in accordance with an embodiment of the invention, are fairly straightforward. It allows the customer to see the wireless Internet transaction through the end user's eyes in terms of their experience when accessing content and conducting transactions from wireless devices. In addition, it allows the customers a method for evaluating and comparing the performance of the wireless networks that are delivering the content. Furthermore, it allows the wireless operators and the content providers solid data to pinpoint bottlenecks and performance problems in the network. Additionally, it provides information to alert staff to critical service failures so corrective action can be taken in a timely manner.

There are a variety of potential measurements that can be taken. Each measurement is referred to as a mission. Some examples of missions include retrieval of a WML page, completion of an e-commerce transaction, receiving pushed data content, performing a secure transaction, and performing benchmarking of different parts of the network by using a component located at the WAP gateway.

There are a variety of methods for inputting requested missions. If the customer wishes, they can discuss their requirements with the system operator and allow the system operator to enter the missions. Alternatively, a user interface in the back end processor allows the customers to enter their own missions over the Internet by entering through the portal.

The parameters for a mission may include at least the following items:
  Type of access—WAP, SMS, Instant Messaging, Push data, and the like.
  Type of Device—WAP, PDA, Pager, wireless modem, and the like.
  Trigger—time of call, location of remote unit, or some combination
  Wireless System—Sprint, Nextel, AT&T, and the like.
  Call Info—Target phone#, URL, type of transaction, etc Mobile or Terr. Originated.

The output of the system can be obtained in a variety of ways. Generally, customers can set up formatted reports that will be generated periodically with the requested data and statistical information. The reports are obtainable in a variety of ways such as viewed using a Web browser, sent as an attachment to e-mail, sent as a file using FTP or some other protocol, or sent via normal mail just to name a few examples. The reports can be arranged in a variety of formats depending on the customer requirements with examples provided in the following figures.

Figure 8A:
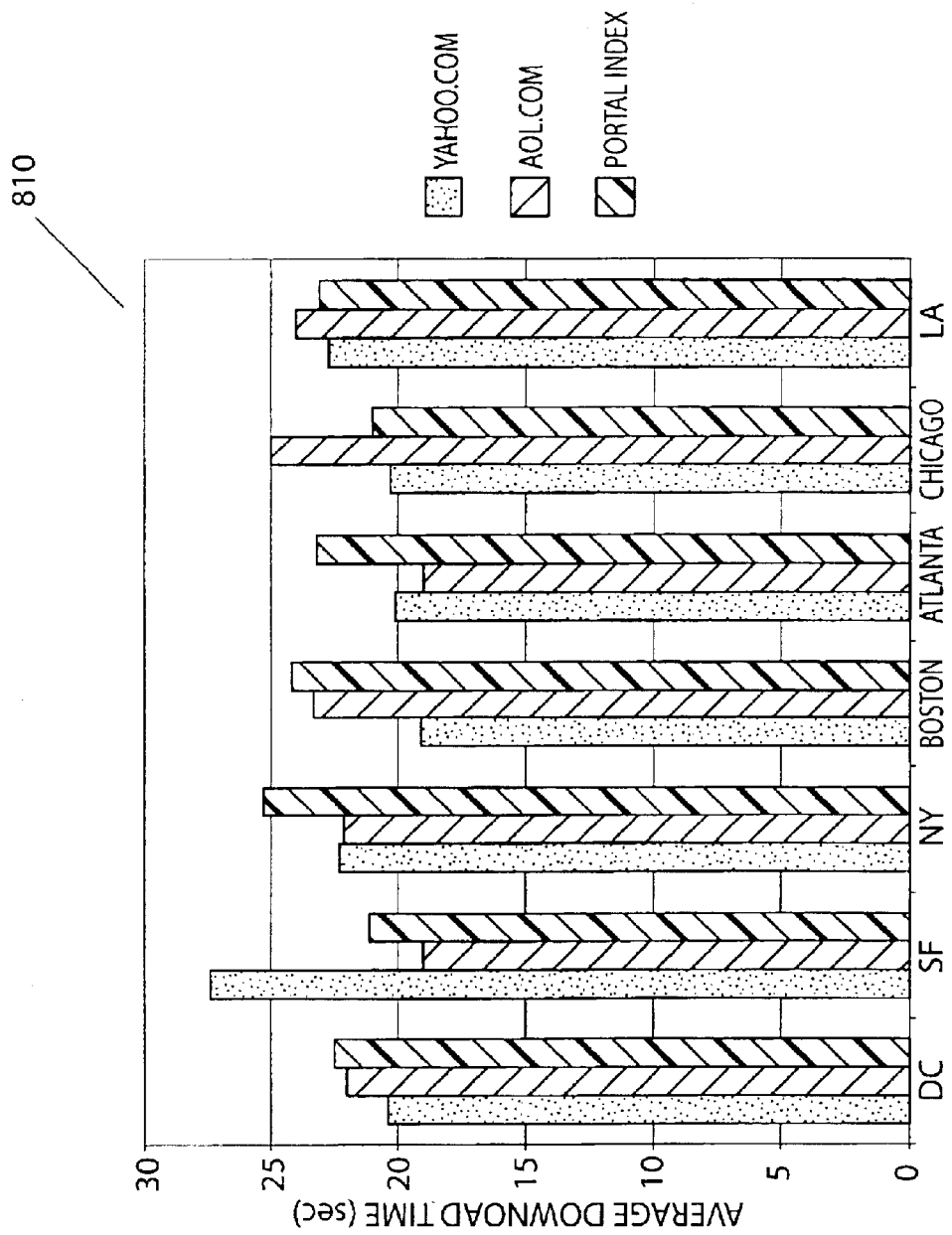
FIG. 8a shows a bar graph output of download times from different portals in accordance with an embodiment of the invention.

FIG. 8a shows a bar graph output 810 of download times from different portals, in accordance with an embodiment of the invention. The y-axis of the bar graph relates to the average download time in seconds and the x-axis relates to the city in which the measurement was performed. The three bars represent measurements for Yahoo, AOL, and a portal index of measurements over all portals. The statistics shown are for all wireless carriers, with a measurement interval of 15 minutes between 6 AM and 12 PM, for the period from Mar. 1, 2000 to Mar. 7, 2000.

FIG. 8b shows a bar graph output 820 of download times across different wireless networks, in accordance with an embodiment of the invention. The y-axis of the bar graph relates to the average download time in seconds and the x-axis relates to the city in which the measurement was performed. The three bars represent measurements for Nextel, Sprint PCS, and AT&T Wireless. The statistics shown are for access to Yahoo, with a measurement interval of 30 minutes between 6 AM and 9 PM, for the period from Mar. 1, 2000 to Mar. 7, 2000.

Figure 8C:
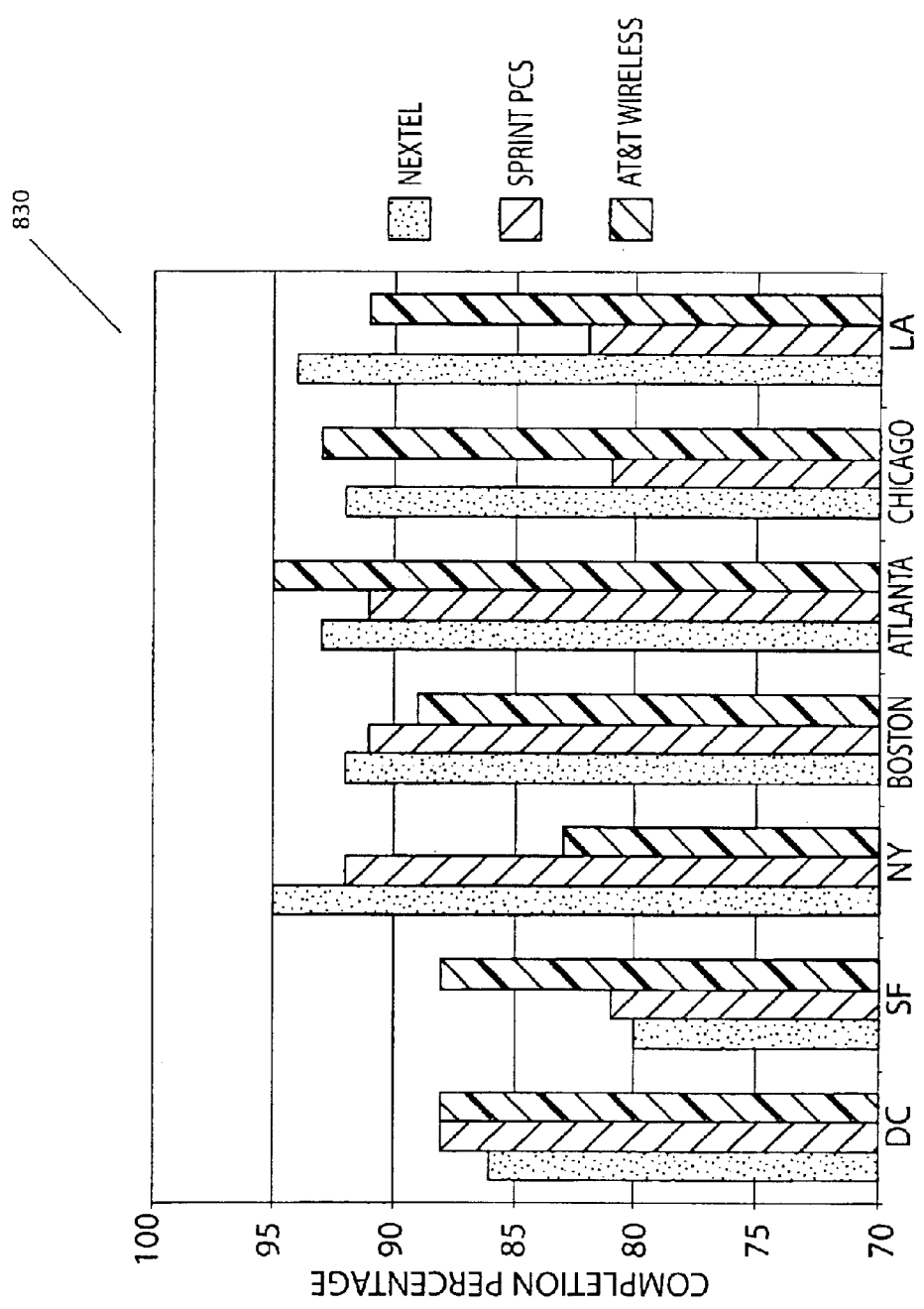
FIG. 8c shows a bar graph output of call completion percentage across different wireless networks in accordance with an embodiment of the invention.

FIG. 8c shows a bar graph output 830 of call completion percentage across different wireless networks, in accordance with an embodiment of the invention. The y-axis of the bar graph relates to the call completion percentage and the x-axis relates to the city in which the measurement was performed. The three bars represent measurements for Nextel, Sprint PCS, and AT&T Wireless. The statistics shown are for access to Yahoo, with a measurement interval of 30 minutes between 6 AM and 9 PM, for the period from Mar. 1, 2000 to Mar. 7, 2000.

Figure 8D:
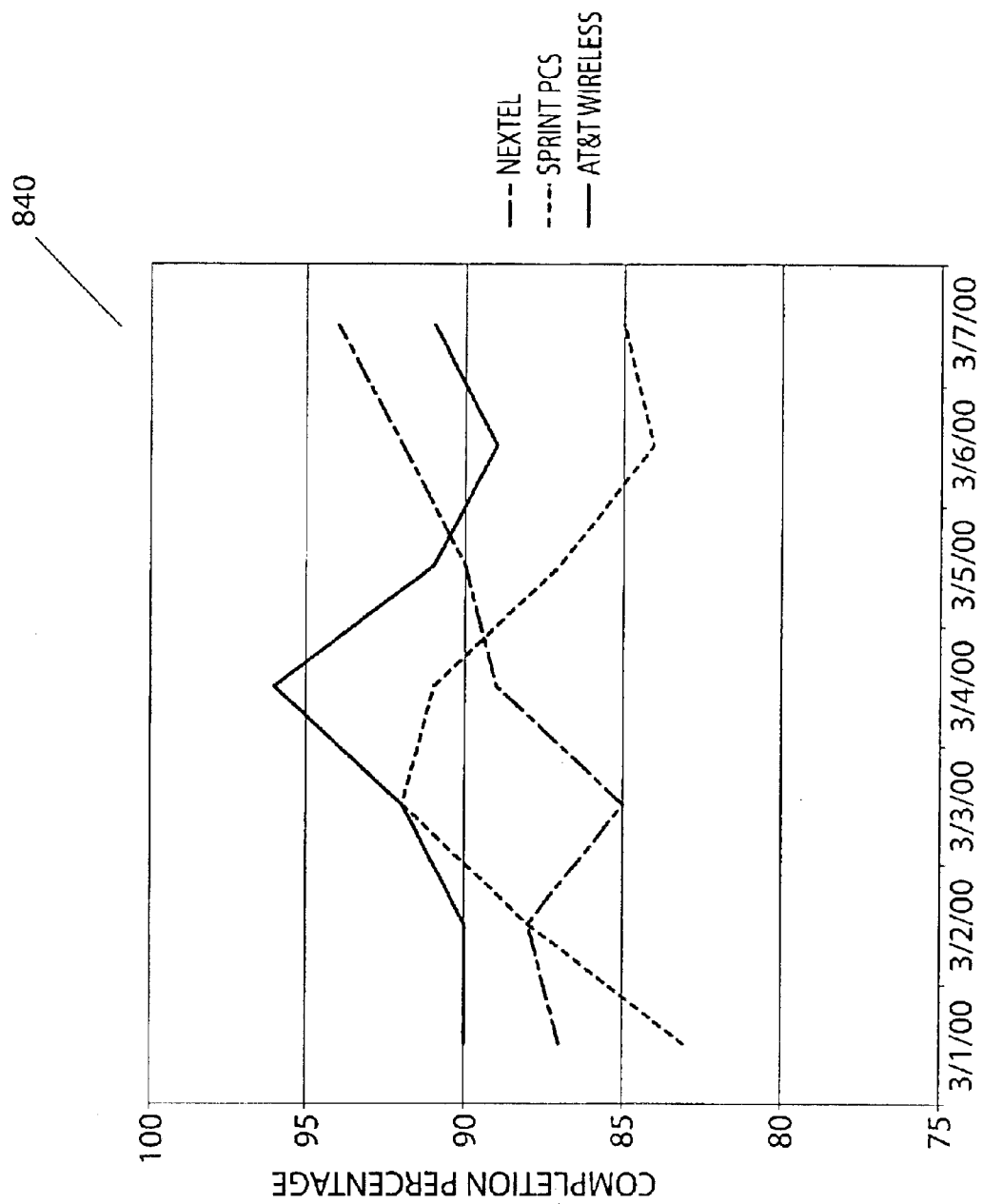
FIG. 8d shows a trending graph output of call completion percentage across different wireless networks in accordance with an embodiment of the invention.

FIG. 8d shows a trending graph output 840 of call completion percentage across different wireless networks, in accordance with an embodiment of the invention. The y-axis of the bar graph relates to the call completion percentage and the x-axis relates to the city in which the measurement was performed. The three bars represent measurements for Nextel, Sprint PCS, and AT&T Wireless. The statistics shown are for access to Yahoo, with a measurement interval of 15 minutes between 6 AM and 9 PM, for the period from Mar. 1, 2000 to Mar. 7, 2000.

Figure 8E:
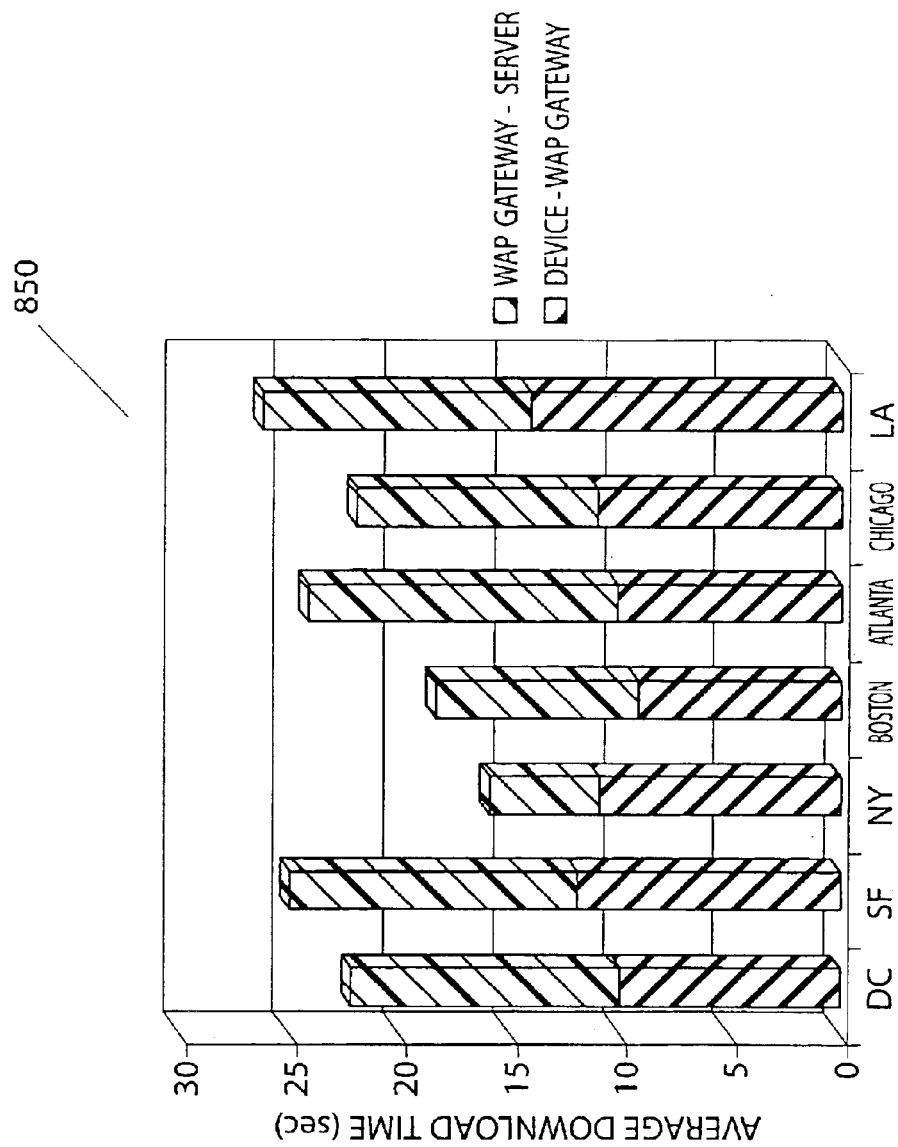
FIG. 8e shows a bar graph output of average download times with a breakdown of the network latency at the WAP gateway in accordance with an embodiment of the invention.

FIG. 8e shows a bar graph output 850 of average download times with a breakdown of the network latency at the WAP gateway, in accordance with an embodiment of the invention. The y-axis of the bar graph relates to the average download time in seconds and the x-axis relates to the city in which the measurement was performed. The bars represent measurements for Nextel with statistics shown for access to Yahoo, with a measurement interval of 60 minutes between 12 PM and 12 PM, for the period from Mar. 3, 2000 to Mar. 7, 2000.

FIG. 8f shows a pie chart 860 of error statistics for wireless access of Yahoo, in accordance with an embodiment of the invention. The sectors of the pie chart show DNS lookup failure, connection timeout, page timeout, content errors, and successful error-free connections. The statistics represent error statistics for all carriers with statistics shown for access to Yahoo, with a measurement interval of 60 minutes between 12 PM and 12 PM, for the period from Mar. 1, 2000 to Mar. 7, 2000.

The present invention has been described in accordance with a number of preferred embodiments. However, it will be understood by those of ordinary skill in the art that various modifications and improvements may be made to the invention as described, without departing from the scope of the invention. The scope of the invention is limited only by the appended claims.

We claim:

1. A method for measuring data quality of service on a communication path between a first node in a traffic wireless network and a second node in a data network, the method comprising:

sending to the first node command information related to data quality of service measurements for at least one of the communications path and the second node;

performing measurements on at least one of the communication path and the second node to produce measurement information in relation to said command information; and receiving response information in relation to said measurement information and said command information.

2. The measuring method of claim 1 wherein said sending step uses a wireless link.

3. The measuring method of claim 1, wherein said sending step uses a CDPD link.

4. The measuring method of claim 1, wherein said sending step uses a wireless LAN link.

5. The measuring method of claim 1, wherein said sending step uses a wired link.

6. The measuring method of claim 1, wherein said receiving step uses a wireless link.

7. The measuring method of claim 1, wherein said receiving step uses a CDPD link.

8. The measuring method of claim 1, wherein said receiving step uses a wireless LAN link.

9. The measuring method of claim 1, wherein said receiving step uses a wired link.

10. The measuring method of claim 1, wherein said performing step produces measurement information related to circuit switched data.

11. The measuring method of claim 1, wherein said performing step produces measurement information related to packet data.

12. The measuring method of claim 1, wherein said performing step produces measurement information related to SMS messages.

13. The measuring method of claim 1, wherein said performing step produces measurement information related to wireless Internet access.

14. The measuring method of claim 1, wherein said performing step produces measurement information related to wireless Internet transactions.

15. The measuring method of claim 14, wherein wireless Internet transactions are e-commerce transactions.

16. The measuring method of claim 1, wherein said performing step produces measurement information related to push data.

17. The measuring method of claim 1, wherein said performing step produces measurement information related to latency.

18. The measuring method of claim 1, wherein said performing step produces measurement information includes Layer 3 network information.

19. The measuring method of claim 1, wherein said performing step produces measurement information includes RF information.

20. The measuring method of claim 1, wherein said performing step produces measurement information includes call connection information.

21. The measuring method of claim 1, wherein said performing step produces measurement information related to iDEN.

22. The measuring method of claim 1, wherein said performing step produces measurement information related to CDMA.

23. The measuring method of claim 1, wherein said performing step produces measurement information related to TDMA.

24. The measuring method of claim 1, wherein said performing step produces measurement information related to AMPS.

25. The measuring method of claim 1, comprising the further step of:
scheduling missions related to said command information.

26. The measuring method of claim 1, comprising the further step of:
generating test traffic related to said measurement information.

27. The measuring method of claim 1, comprising the further step of:
storing said control information at a remote unit.

28. The measuring method of claim 1, comprising the further step of:
storing said measurement information at a remote unit.

29. The measuring method of claim 1, comprising the further step of:
pre-processing said measurement information at a remote unit.

30. The measuring method of claim 1, comprising the further step of:
post-processing said measurement information at a back end processor.

31. The measuring method of claim 1, comprising the further step of:
organizing remote unit data, related to said command information, at a back end processor.

32. The measuring method of claim 1, wherein said sending step includes sending said command information from a back end processor to at least one of a plurality of remote unit.

33. The measuring method of claim 1, wherein said performing step includes performing said measurements using one of a plurality of remote units.

34. The measuring method of claim 1, wherein said receiving step includes receiving said response information at a back end processor from at least one of a plurality of remote units.

35. The measuring method of claim 1, wherein said performing step produces measurement information related to CDPD.

36. The measuring method of claim 1, wherein said performing step produces measurement information related to PDAs.

37. The measuring method of claim 1, wherein said performing step produces measurement information related to GSM.

38. The measuring method of claim 1, wherein said performing step produces measurement information related to private data network traffic.

39. A method for measuring data quality of service in a traffic wireless network comprising:
sending command information related to data quality of service measurements;
performing measurements to produce measurement information in relation to said command information;
receiving response information in relation to said measurement information and said command information; and
monitoring WAP gateway functions.

40. A method for measuring data quality of service in a traffic wireless network comprising:
sending command information related to data quality of service measurements;
performing measurements to produce measurement information in relation to said command information;
receiving response information in relation to said measurement information and said command information; and
benchmarking in relation to a WAP gateway.

41. A measuring system for measuring data quality of service on communication paths between remote nodes in a wireless network and a node on a data network, the system comprising:
a back end processor for controlling the measuring system;
a plurality of remote units, in communication with said back end processor via a control link, acting as remote nodes to perform measurements on at least one of the communication paths and the node on the data network.

42. A measuring system for measuring data quality of service on at least one traffic wireless network, comprising:
a back end processor for controlling the measuring system;
a plurality of remote units, in communication with said back end processor via a control link, for performing measurements on the at least one traffic wireless network; and
a WAP monitor for monitoring WAP gateway functions.

43. A measuring system for measuring data quality of service on at least one traffic wireless network, comprising:
a back end processor for controlling the measuring system;
a plurality of remote units, in communication with said back end processor via a control link, for performing measurements on the at least one traffic wireless network; and
a WAP benchmarker for benchmarking in relation to a WAP gateway.

44. A remote unit, which is one of a plurality of remote units that communicates with a back end processor, for measuring data quality of service on a communication path between a first node in a traffic wireless network and a second node in a data network, the remote unit comprising:
a control unit for controlling said remote unit;
a location unit for providing position information;
a control link modem for communicating via a control link with the back end processor; and
at least one traffic modem for performing measurements on at least one of the communication path and the second node.

45. The remote unit of claim 44, wherein said control unit is a portable computer.

46. The remote unit of claim 44, wherein said control unit is a single board computer.

47. The remote unit of claim 44, wherein said location unit is a GPS receiver.

48. The remote unit of claim 44, wherein said control link modem is a CDPD modem.

49. The remote unit of claim 44, wherein said control link modem is a software-defined radio modem.

50. The remote unit of claim 44, wherein said control link modem is a wired modem.

51. The remote unit of claim 44, wherein each traffic modem of said at least one traffic modem performs measurements on a respective traffic wireless network of the at least one traffic wireless network.

52. The remote unit of claim 44, wherein a respective traffic modem of said at least one traffic modem is a modem module.

53. The remote unit of claim 44, wherein a respective traffic modem of said at least one traffic modem is a cellular phone.

54. The remote unit of claim 44, wherein a respective traffic modem of said at least one traffic modem is a software-defined radio.

55. The remote unit of claim 44, wherein a respective traffic modem of said at least one traffic modem is an iDEN modem.

56. The remote unit of claim 44, wherein a respective traffic modem of said at least one traffic modem is a CDMA modem.

57. The remote unit of claim 44, wherein a respective traffic modem of said at least one traffic modem is a TDMA modem.

58. The remote unit of claim 44, wherein a respective traffic modem of said at least one traffic modem is a GSM modem.

59. The remote unit of claim 44, wherein said measurements are performed on circuit switched data.

60. The remote unit of claim 44, wherein said measurements are performed on packet data.

61. The remote unit of claim 44, wherein said measurements are performed on SMS messages.

62. The remote unit of claim 44, wherein said measurements are performed on wireless Internet access.

63. The remote unit of claim 44, wherein said measurements are performed on wireless Internet transactions.

64. The remote unit of claim 44, wherein said measurements are performed on wireless Internet e-commerce transactions.

65. The remote unit of claim 44, wherein said measurements are performed on push data.

66. The remote unit of claim 44, wherein said measurements include latency measurements.

67. The remote unit of claim 44, wherein said measurements include data reliability.

68. The remote unit of claim 44, wherein said measurements include Layer 3 network information.

69. The remote unit of claim 44, wherein said measurements include RF information.

70. The remote unit of claim 44, wherein said measurements include call connection information.

71. The remote unit of claim 44, wherein each of said plurality of remote units includes a battery backup for providing backup battery power.

72. The remote unit of claim 44, further comprising:
an external storage for storing at least one of said measurements.

73. The remote unit of claim 44, further comprising:
a wireless LAN device for communicating with the back end processor.

74. The remote unit of claim 44, further comprising:
an RF scanner for measuring the at least one traffic wireless network.

75. The remote unit of claim 74, wherein said RF scanner is a software-defined radio.

76. The remote unit of claim 44, wherein said remote unit is stationary.

77. The remote unit of claim 44, wherein said remote unit is mobile.

78. The remote unit of claim 44, wherein said control link is wired.

79. The remote unit of claim 44, wherein said control link is wireless.

80. The remote unit of claim 44, wherein a respective traffic modem of said at least one traffic modem is a PDA modem.

81. The remote unit of claim 44, wherein a respective traffic modem of said at least one traffic modem is a CDPD modem.

82. The remote unit of claim 44, wherein said measurements are performed on PDA traffic.

83. The remote unit of claim 44, wherein said measurements are performed on CDPD traffic.

84. The remote unit of claim 44, wherein said measurements are performed on private data network access.

85. A method for measuring data quality of service on communication paths between plural remote units in a traffic wireless network and a second node in a data network, using a back end processor and the plural remote units, the method comprising:
sending command information from the back end processor to at least two of the plural remote units, the command information being related to data quality of service measurements for at least one of the communication paths and the second node;
performing measurements on at least one of the communication paths and the second node, using the at least two of the plural remote units, to produce measurement information in relation to said command information; and
receiving response information at the back end processor from the at least two of the plural remote units, said response information being in relation to said measurement information and said command information;
wherein said response information provides a measure of data quality of service for at least one of the communication paths and the second node.

86. A method for measuring data quality of service on a communication path between a first node in a traffic wireless network and a second node in a data network, the method comprising:
receiving at the first node command information related to data quality of service measurements for at least one of the communication path and the second node, the command information being sent from a back end processor;
performing one or more measurements of performance on at least one of the communication path and the second node to produce measurement information in relation to said command information; and
sending response information in relation to said measurement information and said command information to the back end processor.

87. A method for producing a measurement result that is indicative of data quality of service on communication paths between plural remote units in a traffic wireless network and a second node on a data network, the method comprising:
sending command information to the plural remote units, said command information being related to data quality of service measurements for at least one of the communication paths and the second node;

receiving response information from the plural remote units, said response information being in relation to said command information and measurements performed on the at least one of the communication paths and the second node via the plural remote units; and generating a measurement result based on said response information.

88. A system for assessing data quality of service on communication paths between remote nodes in a wireless network and a node on a data network, the system comprising:

means for obtaining measurements, at a statistically significant number of locations, of a performance parameter of at least one of the communications paths and the node on the data network; and means for consolidating information indicative of the measurements obtained by the means for obtaining;

wherein the information consolidated by the means for consolidating provides an assessment of data quality of service for the at least one of the communication paths and the node on the data network.

89. The system of claim 88, wherein the means for obtaining measurements comprises plural remote units.

90. The system of claim 89, wherein a portion of the plural remote units are mobile units.

91. The system of claim 89, wherein substantially all of the plural measurement units are mobile units.

92. The system of claim 89, wherein substantially all of the plural measurement units are stationary units.

93. The system of claim 88, wherein the means for consolidating comprises a back end processor.

94. The system of claim 88, wherein the means for obtaining measurements performs the function of obtaining measurements in response to command information received from the means for consolidating.

95. A device for obtaining measurements indicative of data quality of service for at least one of communication paths between the device on a wireless network providing data service and a node on a data network, the device comprising:

a control link modem providing communications with a back end processor;

a traffic modem providing communications via the wireless network;

a location unit providing position information; and a computer, the computer comprising:

a processor in communication with the control link modem and the traffic modem, and being connected to the location unit, and a memory, connected to the processor, bearing software instructions adapted to enable the computer to perform the steps of:

receiving command information from the back end processor;

sending test traffic over one or more of the communication paths from the device on the wireless network to the node on the data network based on the command information received from the back end processor;

receiving response traffic over the wireless network from the node on the data network in reply to the test traffic;

recording measurement information comprising information regarding the test traffic, the response traffic, and location information contemporaneous with the step of receiving response traffic; and sending the recorded measurement information to the back end processor.

96. A device for obtaining measurements indicative of data quality of service for at least one of communication paths between the device on a wireless network providing data service and a node on a data network, the device comprising:

a control link modem providing communications with a back end processor;

a traffic modem providing communications via the wireless network;

a location unit providing position information; and a computer, the computer comprising:

a processor in communication with the control link modem and the traffic modem, and being connected to the location unit, and a memory, connected to the processor, bearing software instructions adapted to enable the computer to perform the steps of:

receiving command information from the back end processor;

receiving test traffic over one or more of the communication paths between the device on the wireless network and the node on the data network;

recording measurement information comprising information regarding the test traffic and location information contemporaneous with the step of receiving test traffic; and sending the recorded measurement information to the back end processor.

97. A device for obtaining measurements indicative of data quality of service for at least one of communication paths between the device on a wireless network providing data service and a node on a data network, the device comprising:

a modem providing communications with a back end processor and providing communications via the wireless network;

a location unit providing position information; and a computer, the computer comprising:

a processor in communication with the modem and being connected to the location unit, and a memory, connected to the processor, bearing software instructions adapted to enable the computer to perform the steps of:

receiving command information from the back end processor;

sending test traffic over one or more of the communication paths from the device on the wireless network to the node on the data network based on the command information received from the back end processor;

receiving response traffic over the wireless network from the node on the data network in reply to the test traffic;

recording measurement information comprising information regarding the test traffic, the response traffic, and location information contemporaneous with the step of receiving response traffic; and sending the recorded measurement information to the back end processor.

98. A device for obtaining measurements indicative of data quality of service for at least one of communication paths between the device on a wireless network providing data service and a node on a data network, the device comprising:

a modem providing communications with a back end processor and providing communications via the wireless network;

a location unit providing position information; and a computer, the computer comprising:
    a processor in communication with the modem and being connected to the location unit, and
    a memory, connected to the processor, bearing software instructions adapted to enable the computer to perform the steps of:
        receiving command information from the back end processor;
        receiving test traffic over one or more of the communication paths between the device on the wireless network and the node on the data network;
        recording measurement information comprising information regarding the test traffic and location information contemporaneous with the step of receiving test traffic; and
        sending the recorded measurement information to the back end processor.

* * * * *